United States Patent
Wakamatsu

(10) Patent No.: US 10,814,118 B2
(45) Date of Patent: Oct. 27, 2020

(54) TRANSDERMAL ABSORPTION SHEET

(71) Applicant: FUJIFILM Corporation, Tokyo (JP)

(72) Inventor: Satoshi Wakamatsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 15/694,423

(22) Filed: Sep. 1, 2017

(65) Prior Publication Data

US 2017/0361081 A1 Dec. 21, 2017

Related U.S. Application Data

(63) Continuation of application No. PCT/JP2016/056003, filed on Feb. 29, 2016.

(30) Foreign Application Priority Data

Mar. 3, 2015 (JP) ................................. 2015-041386

(51) Int. Cl.
*A61M 37/00* (2006.01)
*B29C 41/00* (2006.01)
(Continued)

(52) U.S. Cl.
CPC ........ *A61M 37/0015* (2013.01); *A61M 37/00* (2013.01); *B29C 41/003* (2013.01);
(Continued)

(58) Field of Classification Search
CPC .. A61M 2037/0023; A61M 2037/0046; A61M 2037/0053; A61M 37/00; A61M 37/0015
See application file for complete search history.

(56) References Cited

U.S. PATENT DOCUMENTS 9,968,766 B2   5/2018  Wakamatsu et al.
2003/0009113 A1   1/2003  Olson et al.
(Continued)

FOREIGN PATENT DOCUMENTS

CN   102695543 A   9/2012
DE   102010001667 A1   8/2011
(Continued)

OTHER PUBLICATIONS

Diameter [online] retrieved on Aug. 20, 2019 from: https://www.macmillandictionary.com/dictionary/american/diameter; 2 pages (Year: 2019).*

(Continued)

*Primary Examiner* — Ernst V Arnold
(74) *Attorney, Agent, or Firm* — Birch, Stewart, Kolasch & Birch, LLP

(57) ABSTRACT

Provided is a transdermal absorption sheet capable of improving strength against impact at the time of puncture. A transdermal absorption sheet includes a sheet portion and a plurality of needle-like protruding portions arranged on a first principal surface of the sheet portion, in which the sheet portion has a center portion which is a region in which the plurality of needle-like protruding portions are formed, and an outer edge portion which is a region from the center portion to an end portion, and a maximum thickness of a thickness portion of the outer edge portion is larger than an average thickness of the center portion.

11 Claims, 27 Drawing Sheets

(51) Int. Cl.
  *B29C 41/02*  (2006.01)
  *B29C 41/38*  (2006.01)
  B29K 83/00    (2006.01)
  B29K 105/00   (2006.01)
  B29L 31/00    (2006.01)

(52) U.S. Cl.
  CPC .............. *B29C 41/02* (2013.01); *B29C 41/38* (2013.01); *A61M 2037/0023* (2013.01); *A61M 2037/0046* (2013.01); *A61M 2037/0053* (2013.01); *B29K 2083/00* (2013.01); *B29K 2105/0035* (2013.01); *B29K 2905/08* (2013.01); *B29L 2031/753* (2013.01)

(56) References Cited

U.S. PATENT DOCUMENTS

| | | | |
|---|---|---|---|
| 2006/0030812 | A1 | 2/2006 | Golubovic-Liakopoulos et al. |
| 2008/0200883 | A1 | 8/2008 | Tomono |
| 2008/0269685 | A1 | 10/2008 | Singh et al. |
| 2011/0192562 | A1 | 8/2011 | Motoi et al. |
| 2011/0237925 | A1* | 9/2011 | Yue ..................... A61K 9/0021 600/392 |
| 2012/0078189 | A1 | 3/2012 | Ogawa et al. |
| 2012/0184916 | A1 | 7/2012 | Kobayashi et al. |
| 2014/0272101 | A1 | 9/2014 | Chen et al. |

FOREIGN PATENT DOCUMENTS

| | | | |
|---|---|---|---|
| EP | 2462978 | A1 | 6/2012 |
| JP | 2008-6178 | A | 1/2006 |
| JP | 2009-233808 | A | 10/2009 |
| JP | 2010-142473 | A | 7/2010 |
| JP | 2010-233674 | A | 10/2010 |
| JP | 2011-78617 | A | 4/2011 |
| JP | 2011-206178 | A | 10/2011 |
| JP | 2013-153866 | A | 8/2013 |
| JP | 2013-158601 | A | 8/2013 |
| JP | 2015-16362 | A | 1/2015 |
| JP | 5663792 | B2 | 2/2015 |
| KR | 10-0612891 | B1 | 8/2006 |
| WO | WO 2006/080508 | A1 | 8/2006 |
| WO | WO 2008/020633 | A1 | 2/2008 |
| WO | WO 2008/130587 | A2 | 10/2008 |
| WO | WO 2009/014805 | A2 | 1/2009 |
| WO | WO 2009/079712 | A1 | 7/2009 |
| WO | WO 2011/016230 | A1 | 2/2011 |
| WO | WO 2015/009530 | A1 | 1/2015 |

OTHER PUBLICATIONS

Facing [online] retrieved on Aug. 20, 2019 from: https://www.merriam-webster.com/dictionary/facing; 1 page (Year: 2019).*
Extended European Search Report, dated Feb. 5, 2018, for European Application No. 16758867.2.
Extended European Search Report, dated Jan. 30, 2018, for corresponding European Application No. 16758868.0.
Japanese Office Action, dated Jan. 22, 2018, for corresponding Application No. 2015-041386, with an English machine translation.
International Preliminary Report on Patentability and English Translation of Written Opinion of the International Searching Authority dated Sep. 5, 2017, issued in PCT/JP2016/056002 (Forms PCT/IB/373 and PCT/ISA/237).
International Preliminary Report on Patentability and English Translation of Written Opinion of the International Searching Authority, dated Sep. 5, 2017, issued in PCT/JP2016/056003 (Forms PCT/IB/373 and PCT/ISA/237).
International Search Report dated May 24, 2016, issued in PCT/JP2616/056002 (Form PCT/ISA/210).
International Search Report dated May 31, 2016, issued in PCT/JP2016/056003 (Form PCT/ISA/210).
Japanese Notification of Reasons for Refusal and English translation for Application No. 2015-041386, dated Aug. 23, 2018.
Japanese Office Action dated Sep. 27, 2017, for corresponding Japanese Application No. 2015-041385, with an English translation.
Japanese Decision to Grant a Patent for Japanese Application No. 2015-041385, dated Mar. 20, 2018, with machine translation.
European Communication for counterpart European Application No. 16758868.0, dated Nov. 20, 2019.
Extended European Search Report, dated May 22, 2017, for European Application No. 15792241.0.
International Search Report (Form PCT/ISA/210) dated Jul. 7, 2015, for International Application No. PCT/JP2015/060454, with an English translation.
Kivi, "Air Embolism", URL: https://www.healthline.com/health/air-embolism, Sep. 2015, 12 pages.
Written Opinion of the International Searching Authority(Form PCT/ISA/237), dated Jul. 7, 2015, for International Application No. PCT/JP2015/060454.
U.S. Office Action, dated Jul. 31, 2019, for copending U.S. Appl. No. 15/694,409.
Supplemental Notice of Allowance dated Feb. 3, 2020 in copending U.S. Appl. No. 15/694,409.
U.S. Notice of Allowance for U.S. Appl. No. 15/694,409, dated Dec. 11, 2019.
European Office Action dated Jun. 29, 2020 for Application No. 16758868.0.

\* cited by examiner

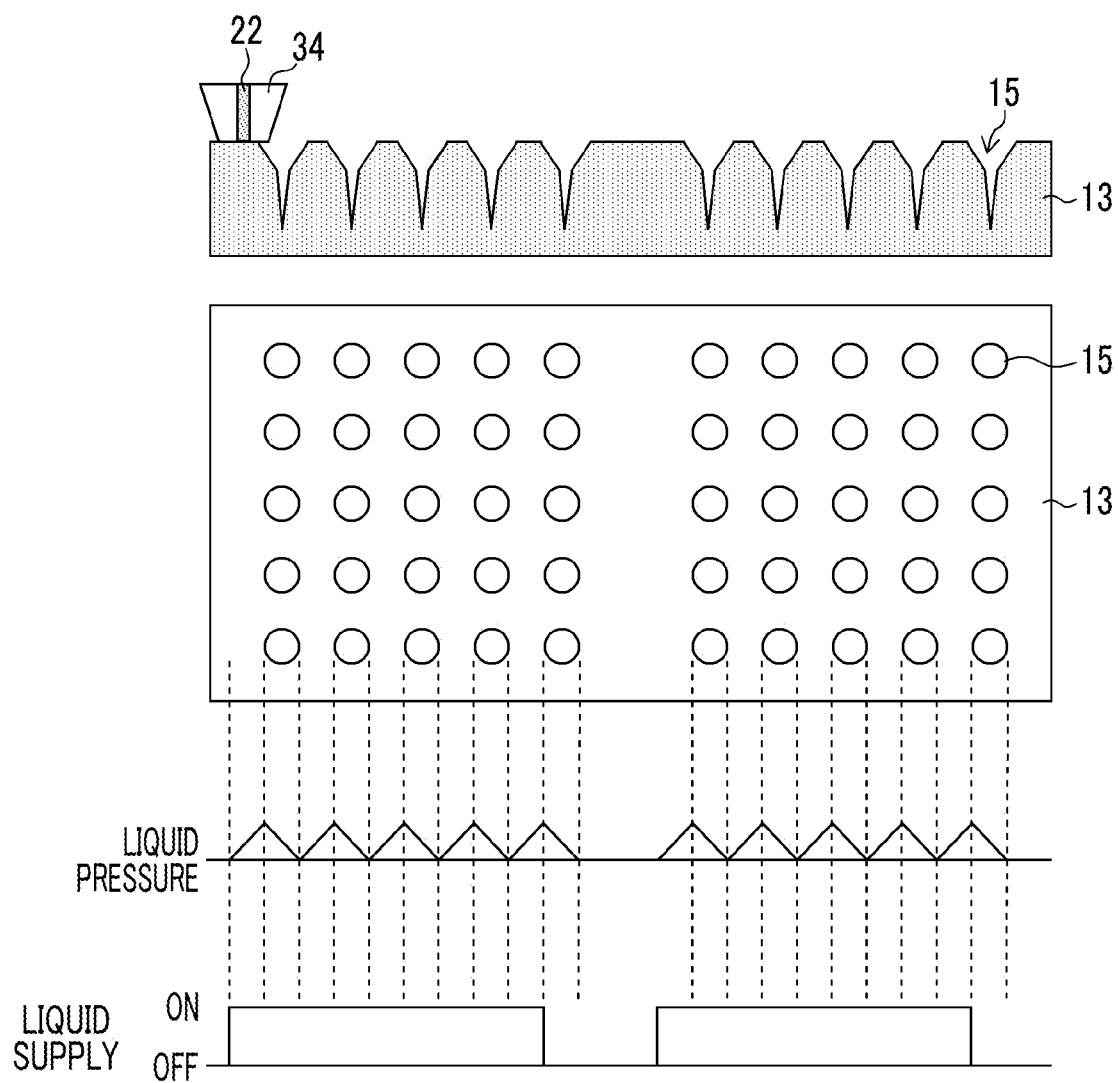

TRANSDERMAL ABSORPTION SHEET

CROSS-REFERENCE TO RELATED APPLICATIONS

This application is a Continuation of PCT International Application No. PCT/JP2016/056003 filed on Feb. 29, 2016, which claims priority under 35 U.S.C. § 119(a) to Japanese Patent Application No. 2015-041386 filed on Mar. 3, 2015. Each of the above applications is hereby expressly incorporated by reference, in their entirety, into the present application.

BACKGROUND OF THE INVENTION

1. Field of the Invention

The present invention relates to a transdermal absorption sheet.

2. Description of the Related Art

In recent years, a transdermal absorption sheet having a plurality of needle-like protruding portions (also referred to as microneedles) containing a drug has been used to deliver a drug into a skin. In general, a drug in needle-like protruding portions is delivered into a skin by attaching a transdermal absorption sheet to a skin and inserting the needle-like protruding portions into the skin.

Various proposals on such a transdermal absorption sheet have been made. For example, JP2008-006178A discloses a method of producing a microneedle sheet (transdermal absorption sheet) having a microneedle array on a surface of a resin polymer including applying a solution in which the resin polymer is dissolved to a stamper to form a microneedle array, drying the solution, laminating and bonding a sheet-like base material on the surface of the dried polymer aggregate, and separating the sheet-like base material and the resin polymer aggregate from the stamper.

In addition, JP2013-158601A discloses a microneedle chip (transdermal absorption sheet) including a support portion, and a needle array region formed by providing a plurality of needles on a surface of the support portion, in which the support portion has a curved shape bent from the back surface thereof toward the surface on which the needle array region is formed.

SUMMARY OF THE INVENTION

In general, a transdermal absorption sheet punctures a subject using a puncture tool (also referred to as an applicator). When a transdermal absorption sheet is used, it is necessary to take out the transdermal absorption sheet from a housing case and attach the transdermal absorption sheet to a puncture tool using an adhesive or the like. In the case of using forceps or the like in the attachment operation, a careless operation may cause damage in the transdermal absorption sheet.

In addition, the puncture tool to which the transdermal absorption sheet is attached is pressed against a skin. The puncture of the transdermal absorption sheet is performed by the puncture tool at a predetermined load and a predetermined speed. In order to reliably and reproducibly puncture the skin with the needle-like protruding portions of the transdermal absorption sheet, it is necessary for the transdermal absorption sheet to have a strength that can endure impact required for puncture.

The transdermal absorption sheet disclosed in JP2008-006178A has a resin polymer having a constant thickness. By forming this resin polymer to be thick, the transdermal absorption sheet can endure impact at the time of puncture. However, by forming the resin polymer to be thick, the drying time of the resin polymer becomes longer. On the other hand, by forming the resin polymer to be thin, the drying time of the resin polymer can be shortened. However, there is a concern of damage to the transdermal absorption sheet due to impact at the time of puncture.

The transdermal absorption sheet disclosed in JP2013-158601A is curved from the surface of a support portion having a fixed thickness to the surface on which a needle array region is formed. Therefore, the skin is pushed out to the outside by the outer edge portion of the support portion at the time of puncture and so-called skin deviation occurs. Due to this skin deviation, a force in a horizontal direction is applied and thus the needles may be bent.

The present invention has been made in consideration of such circumstances and an object thereof is to provide a transdermal absorption sheet capable of improving strength against impact at the time of puncture.

According to an aspect of the present invention, there is provided a transdermal absorption sheet comprising: a sheet-like sheet portion having an end portion and two first and second principal surfaces facing each other; and a plurality of needle-like protruding portions containing a drug arranged on the first principal surface of the sheet portion, in which the sheet portion has a center portion which is a region in which the plurality of needle-like protruding portions are formed and an outer edge portion which is a region from the center portion to the end portion, and a maximum thickness of a thickness portion of the outer edge portion is larger than an average thickness of the center portion.

It is preferable that the maximum thickness is 15 to 5,000 µm, and the average thickness is 10 to 500 µm.

It is preferable that the maximum thickness is 1.5 to 10 times the average thickness.

It is preferable that the thickness portion has the maximum thickness in the narrowest region among a region of the outer edge portion within 5 mm from the end portion, a region of the outer edge portion within 20% of a diameter of the sheet portion from the end portion, and a region of the outer edge portion within 20% of a length of one side of the sheet portion from the end portion.

It is preferable that the thickness portion is provided on the first principal surface and/or the second principal surface of the sheet portion.

It is preferable that an area of the first principal surface of the sheet portion is larger than a projection area of the sheet portion as seen from the first principal surface or the second principal surface.

It is preferable that the sheet portion has a curved shape directed toward the second principal surface from the first principal surface.

It is preferable that the needle-like protruding portion includes a first layer containing a drug, and a second layer not containing a drug.

It is preferable that the second layer and the sheet portion are formed of the same material.

It is preferable that the drug is at least one of peptide, protein, nucleic acid, polysaccharide, a vaccine, a medical compound, or a cosmetic component.

According to the transdermal absorption sheet of the present invention, it is possible to improve strength against impact at the time of puncture.

BRIEF DESCRIPTION OF THE DRAWINGS

FIG. 22 is an illustration showing a relationship between the liquid pressure in the nozzle and the supply of a drug-containing solution.

DESCRIPTION OF THE PREFERRED EMBODIMENTS

Figure 1:
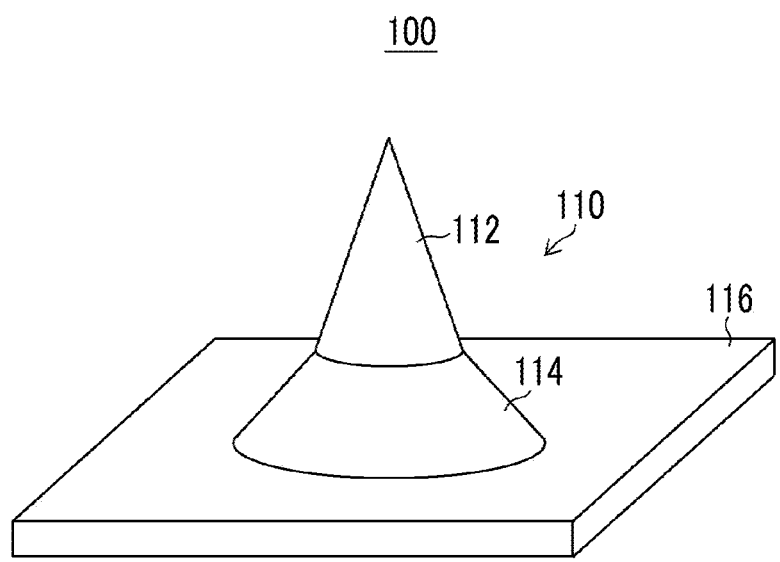
FIG. 1 is a partially enlarged view showing a transdermal absorption sheet having a needle-like protruding portion.

Hereinafter, preferred embodiments of the present invention will be described with reference to the accompanying drawings. The present invention will be described using the following preferred embodiments. Modifications can be made by many methods without departing from the scope of the present invention, and embodiments other than the embodiments can be used. Accordingly, all of the modifications within the scope of the present invention are included in the claims.

In the drawings, components designated by the same reference numeral are similar components having similar functions. Furthermore, in the present specification, in the case in which a numerical range is described using "to", numerical values for an upper limit and a lower limit illustrated with "to" are also included in the numerical range.

Figure 2:
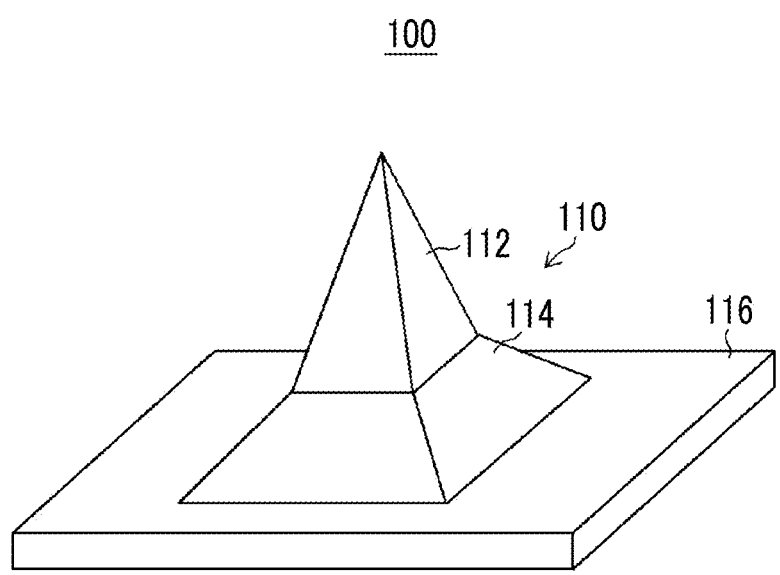
FIG. 2 is a partially enlarged view showing a transdermal absorption sheet having a needle-like protruding portion of another shape.

A transdermal absorption sheet produced in the embodiment will be described. FIGS. 1 and 2 each show a needle-like protruding portion 110 (also referred to as a microneedle) that is a partially enlarged view of a transdermal absorption sheet 100.

The transdermal absorption sheet 100 delivers a drug into the skin by being attached to the skin. As shown in FIG. 1, the transdermal absorption sheet 100 has a tapered-shaped needle portion 112, a frustum portion 114 connected to the needle portion 112, and a sheet-like sheet portion 116 connected to the frustum portion 114. The tapered-shaped needle portion 112 and the frustum portion 114 configure the needle-like protruding portion 110. The term "sheet-like" means a shape in which two facing principal surfaces having a large area (a first principal surface and a second principal surface) have a small thickness and are flat as a whole, and the principal surface is not necessarily flat completely.

A plurality of frustum portions 114 is formed on the surface of the sheet portion 116 (only one frustum portion 114 is shown in FIG. 1). The frustum portion 114 has two bottom surfaces and has a stereoscopic structure surrounded by a pyramidal surface. Out of the two bottom surfaces of the frustum portion 114, a bottom surface (lower base) having a larger area is connected to the sheet portion 116. Out of the two bottom surfaces of the frustum portion 114, a bottom surface (upper base) having a smaller area is connected to the needle portion 112. That is, out of the two bottom surfaces of the frustum portion 114, a bottom surface in a direction in which the bottom surface is separated from the sheet portion 116 has a smaller area.

The needle portion 112 has a gradually tapered shape and the needle portion 112 has a shape having a large area at a bottom surface and having the smallest area at a tip end separated from the bottom surface. Since the bottom surface of the needle portion 112 having a large area is connected to the bottom surface of the frustum portion 114 having a small area, the needle portion 112 has a gradually tapered shape in a direction in which the needle portion is separated from the frustum portion 114. Accordingly, the needle portion 112 has a shape in which the needle-like protruding portion 110 formed of the needle portion and the frustum portion 114 is tapered from the sheet portion 116 to the tip end as a whole. 4 to 2,500 of a plurality of needle-like protruding portions 110 are provided on the sheet portion 116. However, the number of needle-like protruding portions is not limited to the above number.

In FIG. 1, the frustum portion 114 has a truncated cone shape, and the needle portion 112 has a cone shape. The shape of a tip end of the needle portion 112 can be appropriately changed to a curved surface having a radius of curvature of 0.01 μm or more and 50 μm or less, a flat surface, or the like in accordance with the degree of insertion of the needle portion 112 into the skin.

FIG. 2 shows a needle-like protruding portion 110 having another shape. In FIG. 2, the frustum portion 114 has a truncated square pyramid shape and the needle portion 112 has a quadrangular pyramid shape.

Figure 3:
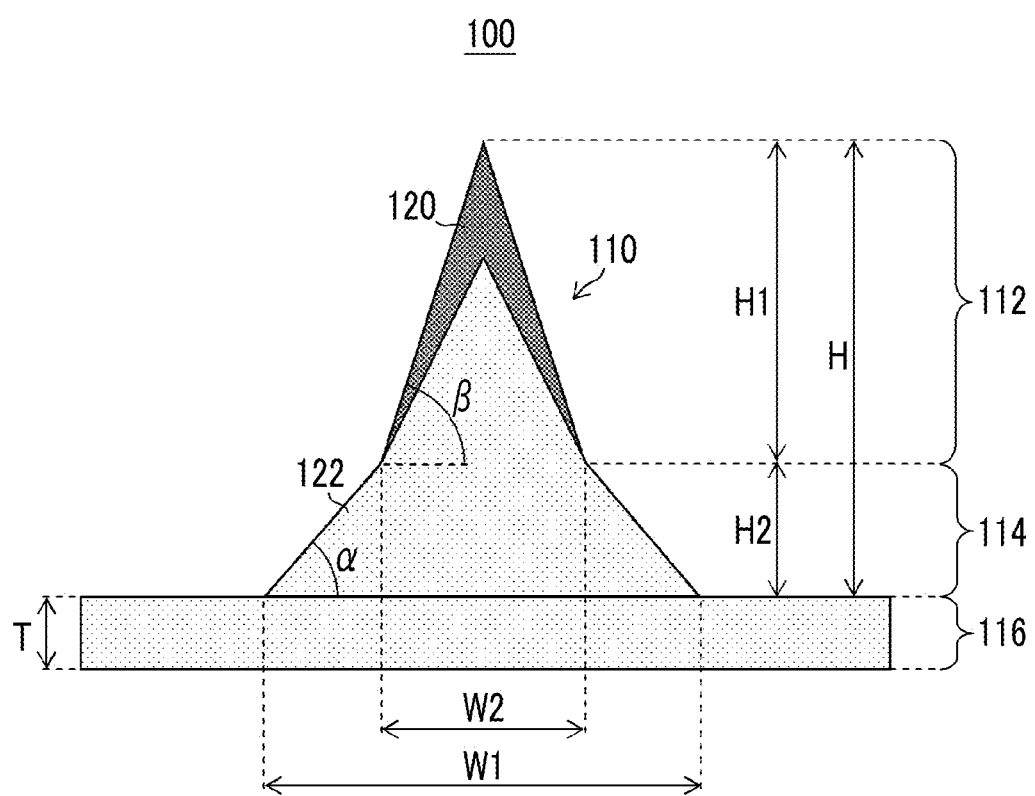
FIG. 3 is a cross-sectional view showing the needle-like protruding portions of the transdermal absorption sheets shown in FIGS. 1 and 2.

FIG. 3 is a cross-sectional view showing the transdermal absorption sheets 100 shown in FIGS. 1 and 2. As shown in FIG. 3, the transdermal absorption sheet 100 is formed of a first layer 120 containing a drug and a second layer 122 not containing a drug.

Here, the expression "containing a drug" means that the transdermal absorption sheet 100 contains a drug in an amount such that the effect of the drug is exhibited in the case in which the transdermal absorption sheet punctures the skin. In addition, the expression "not containing a drug" means that the transdermal absorption sheet does not contain a drug in an amount such that the effect of the drug is exhibited, and the range of the amount of drug includes a range from 0, at which the transdermal absorption sheet does not contain a drug at all, to the amount of the drug in which the effect of the drug is exhibited. The first layer 120 containing a drug is formed at the tip end of the needle-like protruding portion 110 (the tip end of the needle portion 112). The drug can be effectively delivered into the skin by forming the first layer 120 at the tip end of the needle-like protruding portion 110. Hereinafter, the expression "containing a predetermined amount of drug" is referred to as "containing a drug" and the expression "not containing a predetermined amount of drug" is referred to as "not containing a drug" in some cases.

In the part of the needle portion 112 other than the first layer 120, the second layer 122 not containing a drug is formed. The frustum portion 114 is formed of the second layer 122. The sheet portion 116 is formed of the second layer 122. That is, the sheet portion 116 and the second layer 122 are formed of the same material. The distribution of the first layer 120 and the second layer 122 forming the needle portion 112, the frustum portion 114, and the sheet portion 116 can be appropriately set.

The thickness T of the sheet portion 116 is preferably in a range of 10 μm to 2,000 μm and more preferably in a range of 10 μm to 1,000 μm. A width W1 of the bottom surface (lower base) in which the frustum portion 114 and the sheet portion 116 are in contact with each other is preferably in a range of 100 μm to 1,500 μm and more preferably in a range of 100 μm to 1,000 μm. A width W2 of the bottom surface (upper base) in which the frustum portion 114 and the needle portion 112 are in contact with each other is preferably in a range of 100 μm to 1,500 μm and more preferably in a range of 100 μm to 1,000 μm. It is preferable that the width W1 and the width W2 satisfy the relationship of W1>W2 in the above numerical value range.

The height H of the needle-like protruding portion 110 is preferably in a range of 100 μm to 2,000 μm and more preferably in a range of 200 μm to 1.500 μm. In addition, H1/H2 that is a ratio between a height H1 of the needle portion 112 and a height H2 of the frustum portion 114 is preferably in a range of 1 to 10 and more preferably in a range of 1.5 to 8. In addition, the height H2 of the frustum portion 114 is preferably in a range of 10 μm to 1,000 μm.

An angle α formed between the side surface of the frustum portion 114 and a surface parallel with the surface of the sheet portion 116 is preferably in a range of 10° to 60° and more preferably in a range of 20° to 50°. In addition, an angle β formed between the side surface of the needle portion 112 and a surface parallel to the upper base of the frustum portion 114 is preferably in a range of 45° to 85° and more preferably in a range of 60° to 80°.

The angle β may be equal to the angle α but the angle β is preferably equal to or greater than the angle α. This is because the needle-like protruding portion 110 easily punctures the skin.

Figure 4:
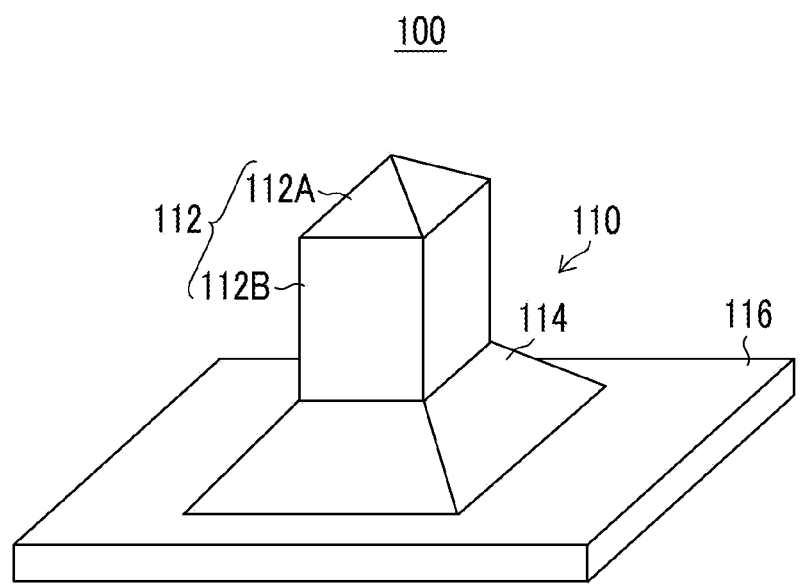
FIG. 4 is a perspective view showing a transdermal absorption sheet having a needle-like protruding portion of another shape.
Figure 5:
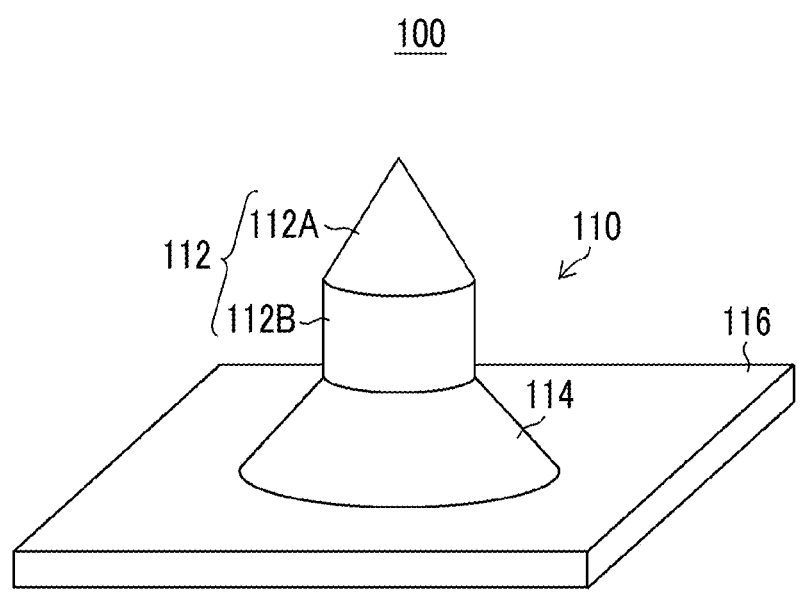
FIG. 5 is a perspective view showing a transdermal absorption sheet having a needle-like protruding portion of another shape.

FIGS. 4 and 5 show needle-like protruding portions 110 having other shapes. The transdermal absorption sheets 100 shown in FIGS. 1 and 4 are the same in shape of the frustum portion 114 but are different in shape of the needle portion 112. Similarly, the transdermal absorption sheets 100 shown in FIGS. 2 and 5 are the same in shape of the frustum portion 114 but are different in shape of the needle portion 112, respectively. Each needle portion 112 shown in FIGS. 4 and 5 has a tapered needle-like portion (tapered tip end portion, tapered tip part) 112A and a cylindrical body portion 112B. The tapered needle-like portion 112A has a shape in which the bottom surface has a wide area and the tip end apart from the bottom surface has the smallest area. The cylindrical body portion 112B has two facing bottom surfaces and the two facing bottom surfaces have almost the same area. The bottom surface of the needle-like portion 112A having a wide area is connected to one bottom surface of the body portion 112B. In addition, the other bottom surface of the body portion 112B is connected to the bottom surface of the frustum portion 114 having a narrow area.

The needle-like portion 112A shown in FIG. 4 has a conical shape and the body portion 112B has a columnar shape. The needle-like portion 112A shown in FIG. 5 has a quadrangular pyramid shape and the body portion 112B has a quadrangular shape.

Since the needle portion 112 has the body portion 112B, the needle portion 112 is formed to have a shape having a fixed cross-sectional area in a direction apart from the frustum portion 114. The tapered needle-like portion 112A of the needle portion 112 has a shape tapered in a direction apart from the body portion 112B. The needle portion 112 has a tapered shape as a whole. According to a degree of insertion of the needle portion 112 into the skin, the shape of the tip end of the needle portion 112 can be appropriately changed to have a curved surface of a radius of curvature of 0.01 µm or more and 50 µm or less, a flat surface, or the like.

Figure 6:
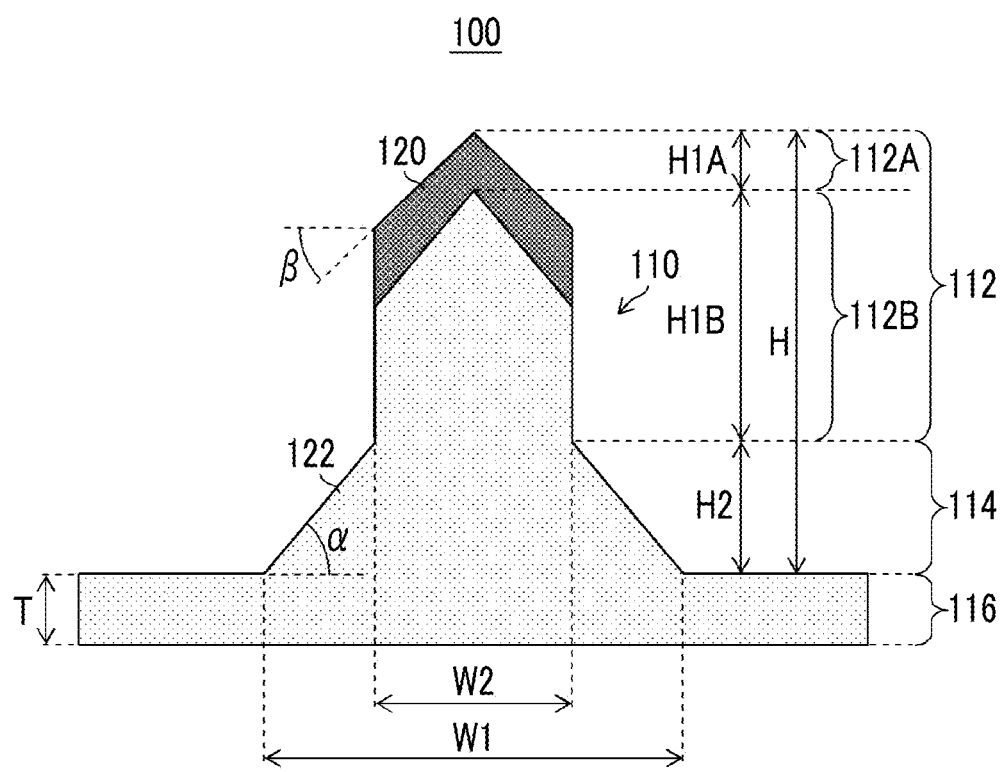
FIG. 6 is a cross-sectional view showing the needle-like protruding portions of the transdermal absorption sheets shown in FIGS. 4 and 5.

FIG. 6 is a cross-sectional view showing the transdermal absorption sheets 100 shown in FIGS. 4 and 5. As shown in FIG. 6, the transdermal absorption sheet 100 is formed of the first layer 120 containing a drug and the second layer 122 not containing a drug. The first layer 120 containing a drug is formed at the tip end of the needle-like protruding portion 110 (the tip end of the needle portion 112). By forming the first layer 120 at the tip end of the needle-like protruding portion 110, the drug can be effectively delivered into the skin.

In the part of the needle portion 112 other than the first layer 120, the second layer 122 not containing a drug is formed. The frustum portion 114 is formed of the second layer 122. The sheet portion 116 is formed of the second layer 122. The distribution of the first layer 120 and the second layer 122 forming the needle portion 112, the frustum portion 114, and the sheet portion 116 can be appropriately set.

The thickness T of the sheet portion 116, the width W1 of the lower base of the frustum portion 114, the width W2 of the upper base of the frustum portion 114, the height H of the needle-like protruding portion 110, and the height H2 of the frustum portion 114 can be set to be the same as the lengths in the transdermal absorption sheet 100 shown in FIG. 3. H1/H2 that is a ratio between the height H1 of the needle portion 112 and the height H2 of the frustum portion 114 can be set to be the same as the ratio in the transdermal absorption sheet 100 shown in FIG. 3.

H1B/H1A that is a ratio between a height H1A of the needle-like portion 112A and a height H1B of the body portion 112B is in a range of 0.1 to 4 and preferably in a range of 0.3 to 2.

The angle α formed between the side surface of the frustum portion 114 and a surface parallel to the surface of the sheet portion 116 is in a range of 10° to 60° and preferably in a range of 20° to 50°. In addition, the angle β formed between the side surface of the needle-like portion 112A and a surface parallel to the bottom surface of the body portion 112B is in a range of 45° to 85° and preferably in a range of 60° to 80°.

The angle β is preferably equal to or greater than the angle α. This is because the needle-like protruding portion 110 is easily inserted into the skin.

In the embodiment, the transdermal absorption sheets 100 having the needle-like protruding portions 110 shown in FIGS. 1, 2, 4, and 5 are described but the shape of the transdermal absorption sheet 100 is not limited to these shapes.

Figure 7A:
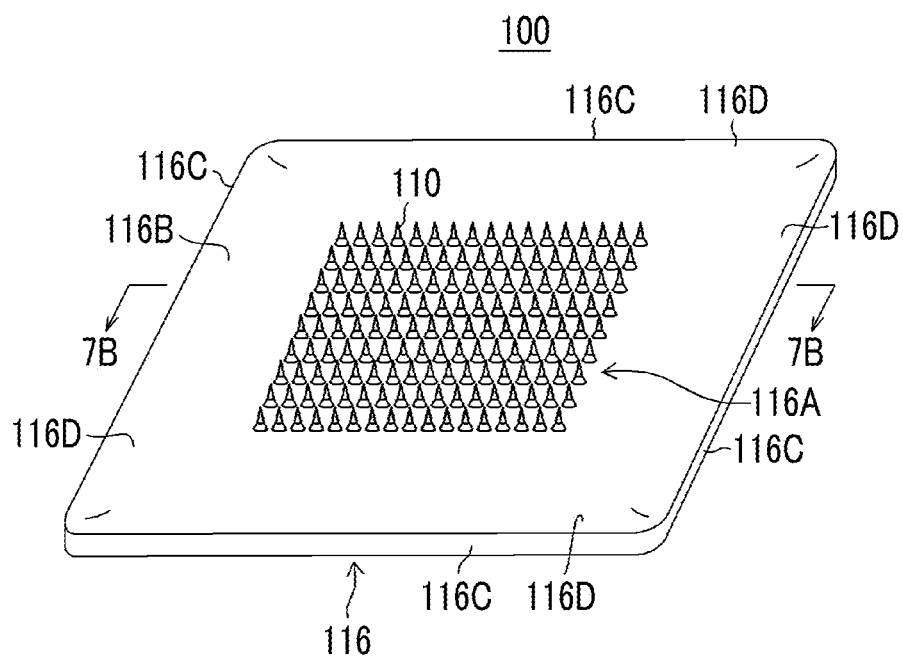
FIG. 7A is a perspective view showing the entire transdermal absorption sheet.

FIG. 7A is a perspective view showing the entire transdermal absorption sheet. As shown in FIG. 7A, the transdermal absorption sheet 100 is constituted of a sheet portion 116 having a first principal surface and a second principal surface, and a plurality of needle-like protruding portions 110 arranged on the first principal surface of the sheet portion 116. The sheet portion 116 has an end portion 116C, and is constituted of a center portion 116A which is a region in which the plurality of needle-like protruding portions 110 are arranged, and an outer edge portion 116B which is a region from the center portion 116A to the end portion 116C. The shape of the sheet portion 116 in plan view is defined by the end portion 116C. The shape of the sheet portion 116 shown in FIG. 7A in plan view is rectangular but may be polygonal, circular, elliptical, or the like. As long as the center portion 116A in which the plurality of needle-like protruding portions 110 can be arranged, and the outer edge portion 116B can be provided in the sheet portion, the shape of the sheet portion 116 is not limited. The transdermal absorption sheet 100 of the embodiment has a thickness portion 116D in the outer edge portion 116B. The thickness portion 116D is a part of which the film thickness is thick in the outer edge portion 116B of the sheet portion 116.

Figure 7B:
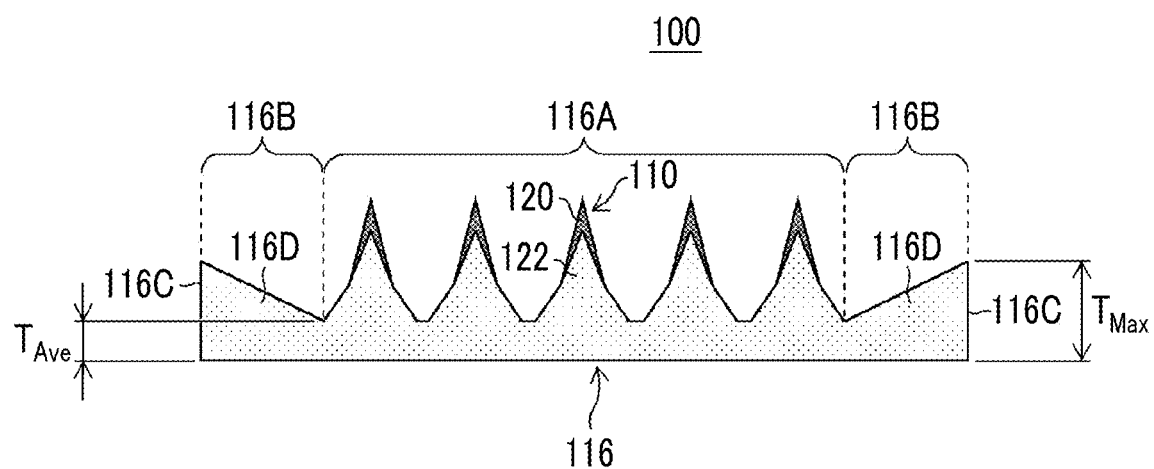
FIG. 7B is a cross-sectional view showing the transdermal absorption sheet.

FIG. 7B is a cross-sectional view taken along the cross sectional line 7B-7B of FIG. 7A. For easy understanding, the number of needle-like protruding portions 110 is reduced and the size of the center portion 116A and the outer edge portion 116B is changed. In the embodiment, in the transdermal absorption sheet 100, the maximum thickness $T_{Max}$ of the thickness portion 116D of the outer edge portion 116B is larger than the average thickness $T_{Ave}$ of the center portion 116A. The maximum thickness $T_{Max}$ of the thickness portion 116D of the outer edge portion 116B is a thickness of the part having the thickest film thickness in the thickness portion 116D of the outer edge portion 116B of the sheet portion 116. In addition, the average thickness $T_{Ave}$ of the center portion 116A is an average thickness of the sheet portion 116 excluding the needle-like protruding portions 110 in the center portion 116A. The maximum thickness $T_{Max}$ of the thickness portion 116D and the average thickness $T_{Ave}$ can be measured by cutting the transdermal absorption sheet in strips and observing the cross section of each piece of the strips with a digital microscope.

The needle-like protruding portion 110 is a part protruding from the sheet portion 116 and is defined as a virtual auxiliary surface in contact with the first principal surface of the sheet portion 116 so that the needle-like protruding portion 110 can be specified.

The thickness portion 116D in FIG. 7B is shaped such that the thickness gradually increases in a direction away from the first principal surface from the center portion 116A to the end portion 116C in sectional view. The thickness portion 116D is formed to have a flat shape in the second principal surface. The thickness portion 116D has the maximum thickness $T_{Max}$ in the end portion 116C.

Figure 8A:
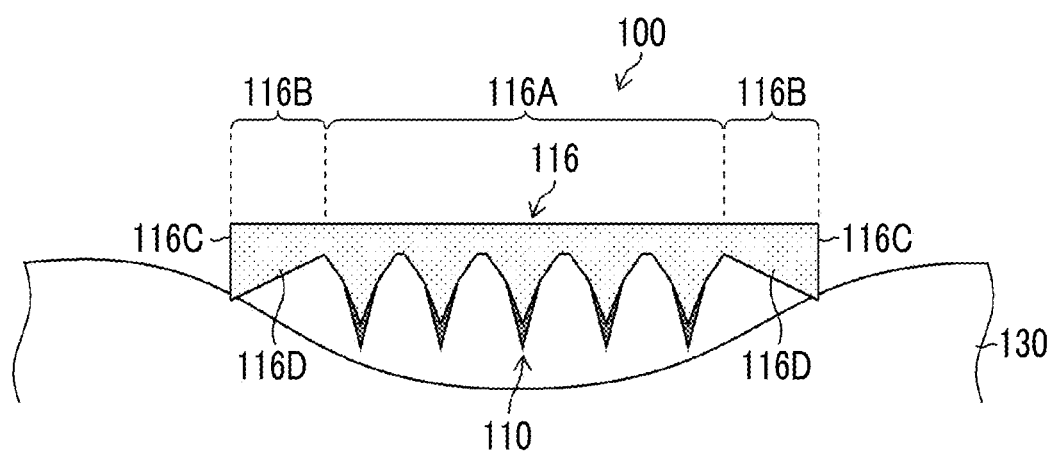
FIG. 8A is an illustration for showing a state in which the transdermal absorption sheet punctures a skin.
Figure 8B:
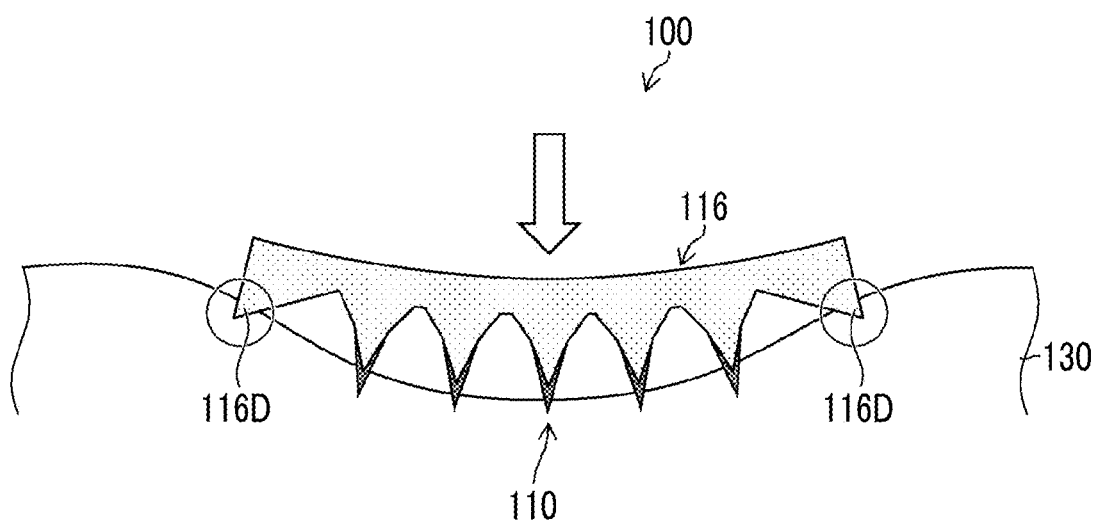
FIG. 8B is an illustration for showing the state in which the transdermal absorption sheet punctures the skin.

FIGS. 8A and 8B are schematic views in the case of puncturing the skin using the transdermal absorption sheet of the embodiment. FIG. 8A shows a state in which the transdermal absorption sheet 100 is brought into tight contact with a skin 130 of a subject. The needle-like protruding portion 110 of the transdermal absorption sheet 100 is positioned to face the skin 130. The first principal surface of the sheet portion 116 is arranged to face the skin 130. Since the transdermal absorption sheet 100 has the thickness portion 116D in the outer edge portion 116B of the sheet portion 116, the thickness portion 116D is brought into contact with the skin 130.

FIG. 8B shows a state in which the transdermal absorption sheet 100 is pressed to the skin 130. The transdermal absorption sheet 100 is pressed to the skin 130 of the subject from the second principal surface of the sheet portion 116. In the case in which the transdermal absorption sheet 100 is pressed, stress is concentrated on the thickness portion 116D. As a result, the transdermal absorption sheet is pushed to the skin 130 by the thickness portion 116D at the position surrounded by the circle and thus the skin 130 can be fixed. Fixing of the skin 130 by the thickness portion 116D can prevent skin deviation caused by pushing out the skin 130 to the outside. Damage of the needle-like protruding portion 110 caused by the skin deviation can be reduced.

For example, in the case in which the sheet portion does not have a thickness portion having a fixed thickness and the entire shape is flat, the puncture pressure of the center portion in which the needle-like protruding portions are arranged is reduced and thus the puncture pressure may easily become uneven. In addition, in the case in which the sheet portion does not have a thickness portion having a fixed thickness and the entire shape is a shape protruding toward the skin, pressing of the transdermal absorption sheet to the skin side may cause skin deviation so that there is a concern that the needle-like protruding portions may be bent.

Since the sheet portion has the thickness portion 116D in the outer edge portion 116B as shown in the embodiment, the above concern can be avoided.

Further, by providing the thickness portion 116D in the outer edge portion 116B, even in the case in which the center portion 116A is made thin, the transdermal absorption sheet 100 can be prevented from being damaged during handling before puncture. In the operation of attaching the transdermal absorption sheet to an applicator, for example, it is possible to avoid a risk of damaging the transdermal absorption sheet 100 by pinching the thickness portion 116D with forceps.

It is preferable that the average thickness $T_{Ave}$ of the center portion 116A and the maximum thickness $T_{Max}$ of the thickness portion 116D of the sheet portion 116 have the following relationship.

It is preferable that the average thickness $T_{Ave}$ of the center portion 116A is 10 μm to 500 μm and the maximum thickness $T_{Max}$ of the thickness portion 116D is 15 μm to 5,000 μm. In addition, it is more preferable that the average thickness $T_{Ave}$ of the center portion 116A is 20 μm to 250 μm and the maximum thickness $T_{Max}$ of the thickness portion 116D is 30 μm to 2,500 μm. It is still more preferable that the average thickness $T_{Ave}$ of the center portion 116A is 50 μm to 100 μm and the maximum thickness $T_{Max}$ of the thickness portion 116D is 75 μm to 1,000 μm.

In the above relationship between the average thickness $T_{Ave}$ of the center portion 116A and the maximum thickness $T_{Max}$ of the thickness portion 116D, it is more preferable that the maximum thickness $T_{Max}$ of the thickness portion 116D is 1.5 times to 10 times the average thickness $T_{Ave}$ of the center portion 116A.

By setting the relationship between the average thickness $T_{Ave}$ of the center portion 116A and the maximum thickness $T_{Max}$ of the thickness portion 116D of the sheet portion 116 as described above, a risk of damaging the transdermal absorption sheet 100 by impact during handling before puncture and during puncture can be more effectively reduced.

It is preferable that the thickness portion 116D has the maximum thickness $T_{Max}$ in the narrowest region among the region of the outer edge portion 116B within 5 mm from the end portion 116C, the region of the outer edge portion 116B within 20% of the length of one side of the sheet portion 116 from the end portion 116C, and the region of the outer edge portion 116B within 20% of the diameter of the sheet portion 116 from the end portion 116C. By providing the thickness portion 116D on the side close to the end portion 116C of the sheet portion 116, skin deviation can be more effectively prevented.

In addition, it is preferable that the thickness portion is provided in a range of 80% to 100% of the entire circumference of the outer edge portion 116B along the end portion 116C of the sheet portion 116 in the case in which the thickness portion 116D is provided in the outer edge portion 116B. Here, the 100% refers to a case in which the thickness portion 116D is continuously formed along the end portion 116C. In the case in which the thickness portion 116D is provided less than 100% of the entire circumference of the outer edge portion 116B, it is preferable that the thickness portion 116D is provided at three or more places of the outer edge portion 116B in a divided manner. By providing the thickness portion 116D at three or more places in a divided manner, the length of a region not having the thickness portion 116D can be reduced. That is, it is possible to avoid a risk of skin deviation by providing the thickness portion 116D in the outer edge portion 116B uniformly as much as possible.

Figure 9A:
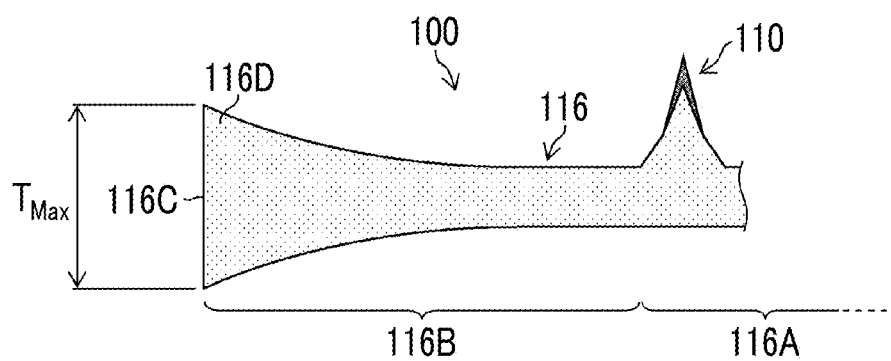
FIG. 9A is a partial cross-sectional view of a transdermal absorption sheet.

FIGS. 9A to 9E are cross-sectional views showing thickness portions of other shapes. As shown in FIG. 9A, the outer edge portion 116B has the same thickness as the thickness of the center portion 116A from the center portion 116A to the end portion 116C, and as approaching the end portion 116C, the thickness portion 116D is shaped such that the thickness gradually increases in a direction away from the first principal surface and the second principal surface. The thickness portion 116D has the maximum thickness $T_{Max}$ in the end portion 116C.

Figure 9B:
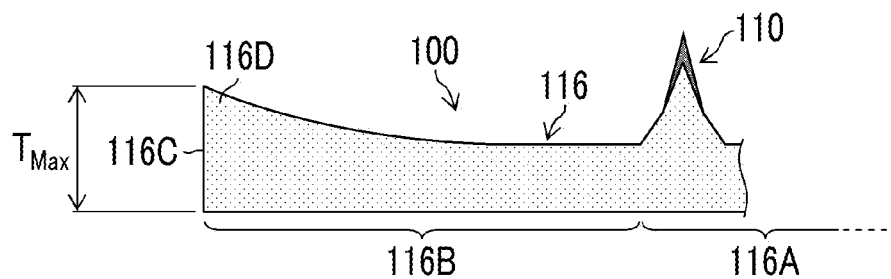
FIG. 9B is a partial cross-sectional view of a transdermal absorption sheet.

As shown in FIG. 9B, the outer edge portion 116B has the same thickness as the center portion 116A from the center portion 116A to the end portion 116C. As approaching the end portion 116C, the thickness portion 116D is shaped such that the thickness gradually increases in a direction away from the first principal surface. The thickness portion 116D has a flat shape in the second principal surface. The thickness portion 116D has the maximum thickness $T_{Max}$ in the end portion 116C.

Figure 9C:
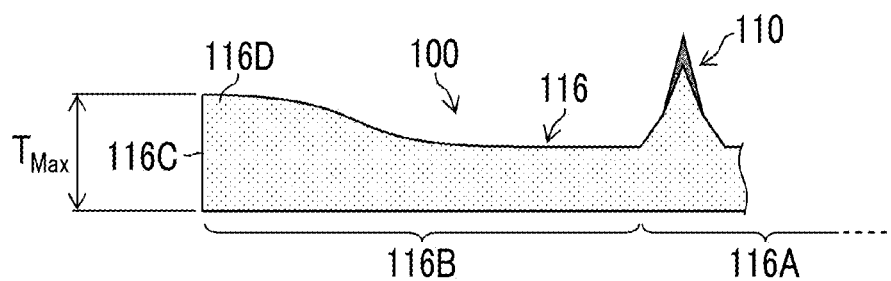
FIG. 9C is a partial cross-sectional view of a transdermal absorption sheet.

As shown in FIG. 9C, the outer edge portion 116B has the same thickness as the thickness of the center portion 116A from the center portion 116A to the end portion 116C. As approaching the end portion 116C, the thickness portion 116D is shaped such that the thickness gradually increases in a direction away from the first principal surface. In FIG. 9C, since the rate of increasing the thickness of the thickness portion 116D decreases as approaching the end portion 116C, a gentle slope is formed compared to FIG. 9B. The thickness portion 116D has a flat shape in the second principal surface. The thickness portion 116D has the maximum thickness $T_{Max}$ in the end portion 116C.

Figure 9D:
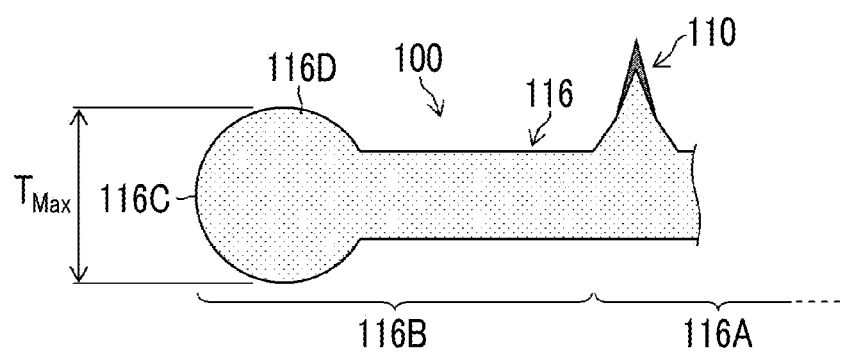
FIG. 9D is a partial cross-sectional view of a transdermal absorption sheet.

As shown in FIG. 9D, the outer edge portion 116B has the same thickness as the thickness of the center portion 116A from the center portion 116A to the end portion 116C. The sheet portion has a thickness portion 116D having a substantially circular cross section on the end portion 116C side. The sheet portion 116 has the maximum thickness in the thickness portion 116D. The maximum thickness $T_{Max}$ of the thickness portion 116D the same as the length of the diameter of the outer edge portion 116B parallel with the thickness direction.

Figure 9E:
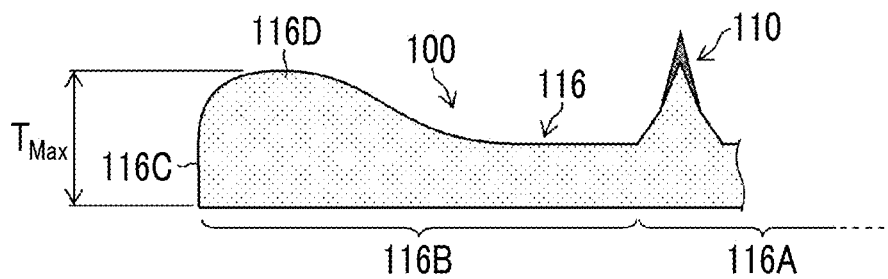
FIG. 9E is a partial cross-sectional view of a transdermal absorption sheet.

As shown in FIG. 9E, the outer edge portion 116B has the same thickness as the thickness of the center portion 116A from the center portion 116A to the end portion 116C. The sheet portion has a thickness portion 116D having a substantially semicircular cross section on the end portion 116C side. The thickness portion 116D has a flat shape in the second principal surface. The sheet portion 116 has the maximum thickness in the thickness portion 116D. The maximum thickness $T_{Max}$ of the thickness portion 116D is the same as the length of the radius of the outer edge portion 116B parallel with the thickness direction.

In FIGS. 9A to 9E, the shapes of the thickness portion 116D are exemplified but is not limited to these shapes. In addition, in the thickness portions 116D shown in FIGS. 9B, 9C, and 9E, the second principal surface of the sheet portion 116 is flat and a part in which the film thickness is thick is provided on the first principal surface side. However, there is no limitation thereto. The first principal surface of the sheet portion 116 may be flat, a part in which the film thickness is thick may be provided on the second principal surface side, and the part in which the film thickness is thick may be provided on the first principal surface and the second principal surface of the sheet portion 116. That is, the thickness portion 116D can be provided on the first principal surface and/or the second principal surface of the sheet portion 116.

Figure 10A:
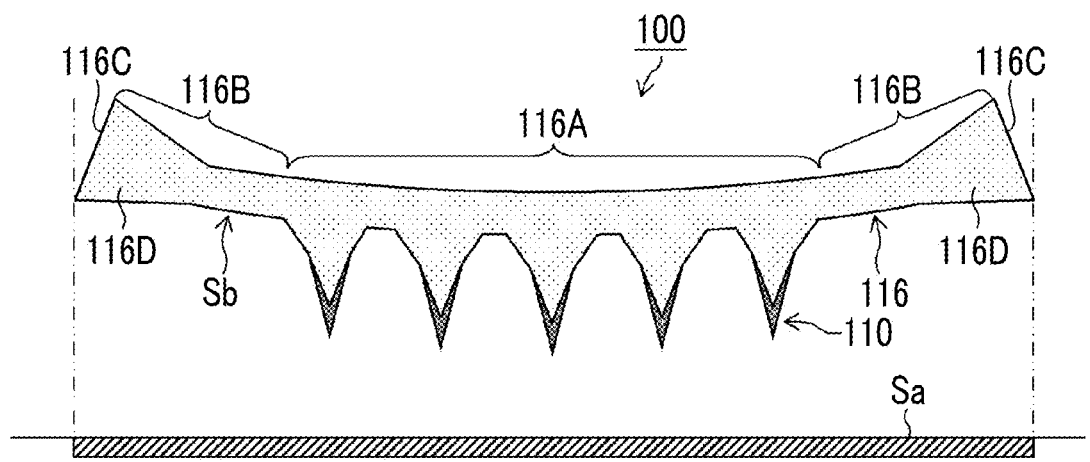
FIG. 10A is a cross-sectional view showing another embodiment of the transdermal absorption sheet.
Figure 10B:
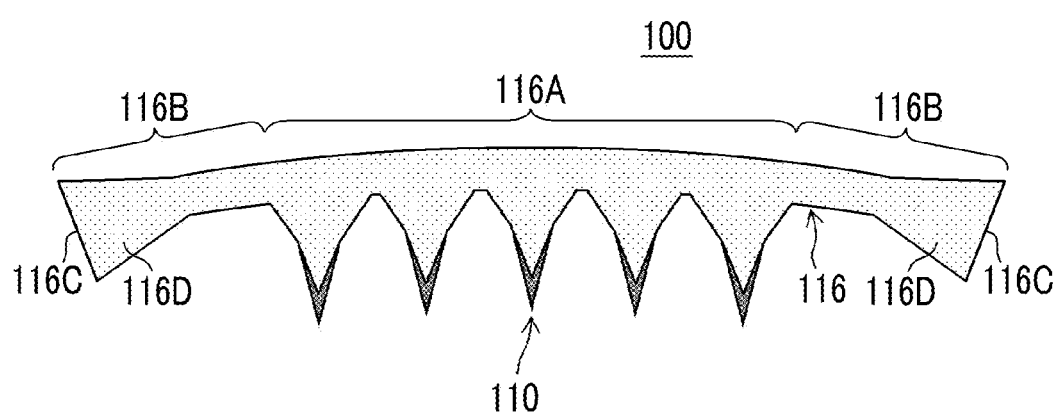
FIG. 10B is a cross-sectional view showing another embodiment of the transdermal absorption sheet.
Figure 10C:
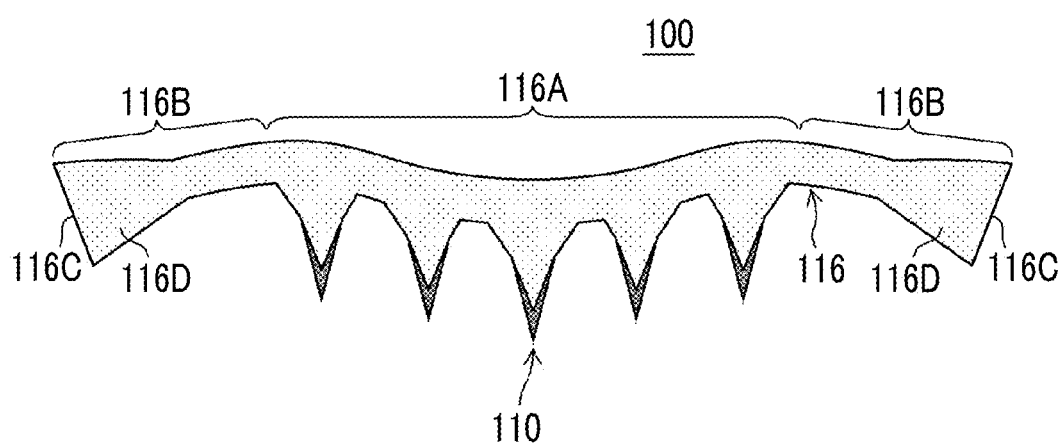
FIG. 10C is a cross-sectional view showing another embodiment of the transdermal absorption sheet.

FIGS. 10A to 10C are cross-sectional views of other embodiments of the transdermal absorption sheet. The transdermal absorption sheet 100 shown in FIG. 10A has the sheet portion 116, and the needle-like protruding portions 110 arranged on the first principal surface of the sheet portion 116. In the outer edge portion 116B of the sheet portion 116, the thickness portion 116D is provided. The thickness portion 116D is provided on the first principal surface and the second principal surface of the sheet portion 116. The transdermal absorption sheet 100 is configured such that an area Sb of the first principal surface of the sheet portion 116 having the needle-like protruding portions 110 is larger than a projection area Sa as seen from the second principal surface in the case of providing the transdermal absorption sheet 100 on the same plane. The projection area Sa means a projection area as seen from the first principal surface or the second principal surface. The area Sb of the first principal surface of the sheet portion 116 means the surface area of the first principal surface after the needle-like protruding portions 110 are removed from the sheet portion 116. The projection area Sa can be obtained using a measurement projector (Japanese Industrial Standard (JIS): JIS B 7184). In addition, the area Sb of the first principal surface of the sheet portion 116 can be obtained by calculating the surface area of the part excluding the needle-like protruding portions 110 from the surface shape data of the first principal surface of the transdermal absorption sheet 100 obtained using an apparatus such as a three-dimensional shape measuring machine or a three-dimensional scanner and adding the bottom area of the excluded needle-like protruding portions to the calculated surface area.

By making the area Sb of the first principal surface of the sheet portion 116 larger than the projection area Sa, in the case of puncture, the sheet portion 116 is easily deformed so as to follow the uneven surface shape of the skin. That is, it is possible to improve the followability of the surface shape of the skin and puncturability. As a result, in the case in which the transdermal absorption sheet 100 is pressed, the puncture pressure to be applied to each needle-like protruding portion 110 can be made uniform. Regarding Sb/Sa which is a ratio between the area Sb of the first principal surface and the projection area Sa, Sb/Sa is preferably 1.0001 to 1.25, Sb/Sa is more preferably 1.0005 to 1.1, and Sb/Sa is still more preferably 1.001 to 1.02.

Since the sheet portion 116 of the transdermal absorption sheet 100 has a curved shape from the second principal surface to the first principal surface in FIG. 10A, in the case of puncture, the needle-like protruding portions 110 can puncture the skin more deeply. The curved shape directed toward the first principal surface from the second principal surface means a curved shape bent toward the first principal surface from the second principal surface.

The transdermal absorption sheet 100 shown in FIG. 10B has the sheet portion 116, the needle-like protruding portions 110 arranged on the first principal surface of the sheet portion 116, and the thickness portion 116D provided in the outer edge portion 116E of the sheet portion 116 as in FIG. 10A. The sheet portion 116 of the transdermal absorption sheet 100 has a curved shape directed toward the second principal surface from the first principal surface. The curved shape from the first principal surface to the second principal surface means a curved shape directed bent the second principal surface from the first principal surface.

Since the sheet portion 116 has a curved shape directed toward the second principal surface from the first principal surface, in the case of puncture, the thickness portion 116D can be inserted into the skin more deeply and the puncture pressure to the needle-like protruding portions 110 caused by the elasticity of the skin can be made uniform.

The transdermal absorption sheet 100 shown in FIG. 10C has the sheet portion 116, the needle-like protruding portions 110 arranged on the first principal surface of the sheet portion 116, and the thickness portion 116D provided in the outer edge portion 116B of the sheet portion 116 as in FIG. 10A. The outer edge portion 116B of the sheet portion 116 of the transdermal absorption sheet 100 has a curved shape directed toward the second principal surface from the first principal surface, and the center portion 116A of the sheet portion 116 has a curved shape directed toward the second principal surface from the first principal surface.

Since Sb/Sa which is a ratio between the area Sb of the first principal surface and the projection area Sa can be increased in the transdermal absorption sheet 100 shown in FIG. 10C, the puncturability of the transdermal absorption sheet 100 can be improved.

The sheet portion 116 has a substantially flat shape or curved shape, and the inscribed circle in the projection shape as seen from the first principal surface and the second principal surface in the case of providing the transdermal absorption sheet 100 on the same plane preferably has a diameter of 10 mm to 50 mm, more preferably has a diameter of 10 mm to 40 mm, and still more preferably has a diameter of 10 mm to 30 mm.

(Mold)

Figure 11A:
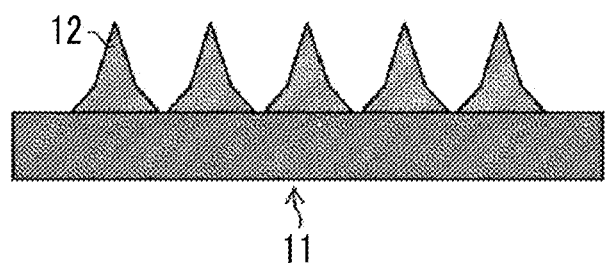
FIG. 11A is a step view showing a method of producing a mold.
Figure 11B:
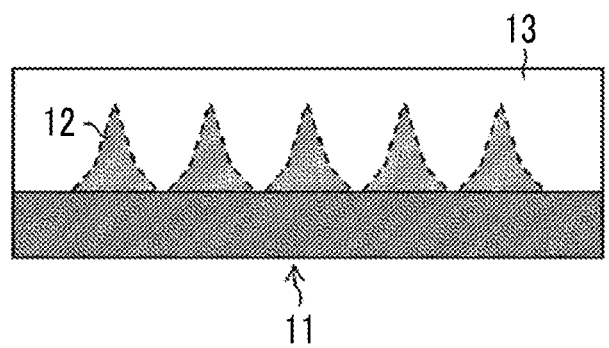
FIG. 11B is a step view showing the method of producing a mold.
Figure 11C:
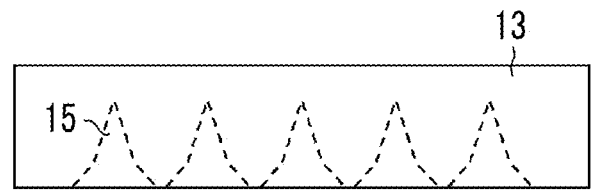
FIG. 11C is a step view showing the method of producing a mold.

FIGS. 11A to 11C are step views showing a step of producing a mold (form).

As shown in FIG. 11A, first, an original plate for producing a mold for producing a transdermal absorption sheet is produced.

There are two kinds of methods of producing the original plate 11. The first method includes applying a photo resist to a Si substrate, and exposing and developing the photo resist. Then, etching by reactive ion etching (RIE) or the like is performed to produce a plurality of protruding portions 12, each having the same shape as the needle-like protruding portion of the transdermal absorption sheet, in arrays on the surface of the original plate 11. In addition, in the case of performing etching such as RIE to form the protruding portion 12 on the surface of the original plate 11, the protruding portion 12 can be formed by performing etching from an oblique direction while rotating the Si substrate.

As the second method, there is a method including processing a metal substrate of stainless steel, an aluminum alloy, Ni, or the like using a cutting tool such as a diamond bite to produce a plurality of protruding portions 12 in arrays on the surface of the original plate 11.

Next, as shown in FIG. 11B, a mold 13 is produced using the original plate 11. In order to produce a normal mold 13, a method using Ni electroforming or the like is generally used. Since the original plate 11 has the protruding portions 12 having a conical shape with a sharp tip end or a pyramid shape (for example, a quadrangular pyramid shape), the shape of the original plate 11 is accurately transferred to the mold 13, and the mold 13 can be peeled off from the original plate 11. Four methods that make possible to accurately produce the mold 13 at a low cost are considered.

The first method is a method in which a silicone resin obtained by adding a curing agent to polydimethylsiloxane (PDMS, for example, SYLGARD 184, manufactured by Dow Corning Corporation) is poured into the original plate 11 and cured by a heating treatment at 100° C., and then the mold 13 is peeled off from the original plate 11. The second method is a method in which an ultraviolet curable resin that is curable by ultraviolet irradiation is poured into the original plate 11 and irradiated with ultraviolet light in a nitrogen atmosphere, and then the mold 13 is peeled off from the original plate 11. The third method is a method in which a material obtained by dissolving a plastic resin such as polystyrene or polymethylmethacrylate (PMMA) in an organic solvent is poured into the original plate 11 which has been coated with a release agent, and is dried to volatilize the organic solvent for curing, and then the mold 13 is peeled off from the original plate 11. The fourth method is a method in which an inverted article is made by Ni electroforming.

In this manner, the mold 13 in which the needle-like recessed portions 15 having an inverted shape of the protruding portion 12 of the original plate 11 are arranged two-dimensionally is produced. The mold 13 produced in this manner is shown in FIG. 11C. Since the shape of the protruding portion 12 of the original plate 11 is the same as the shape of the needle-like protruding portion of the transdermal absorption sheet, as shown in FIG. 11C, the mold 13 having the plurality of needle-like recessed portions corresponding to the inverted shape of the needle-like protruding portion of the transdermal absorption sheet is produced. In addition, in any of the above three methods, the mold 13 can be easily produced any number of times.

Figure 12A:
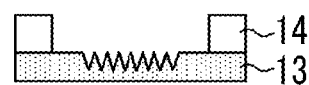
FIG. 12A is a cross-sectional view of a mold provided with a frame.
Figure 12B:
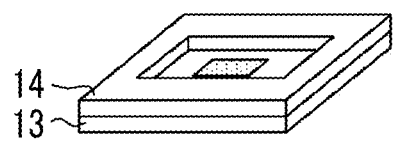
FIG. 12B is a perspective view of the mold provided with the frame.
Figure 12C:
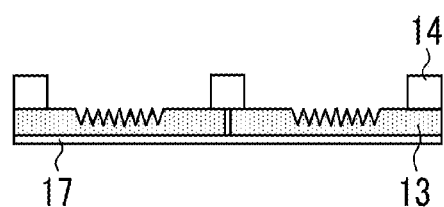
FIG. 12C is a cross-sectional view of the mold provided with the frame.
Figure 12D:
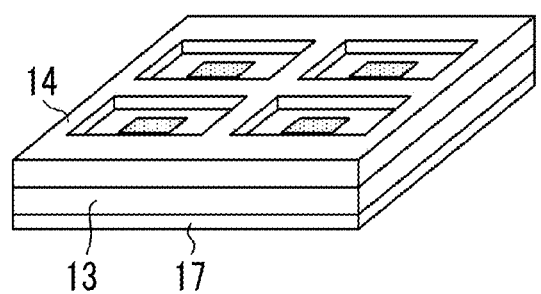
FIG. 12D is a perspective view of the mold provided with the frame.

FIGS. 12A to 12D are views in which a frame 14 is installed on the mold 13 produced in FIG. 11C. FIGS. 12A and 12B are views in which the frame is provided at the periphery of the surface of the mold 13. FIGS. 12C and 12D are views in which the frame 14 is provided at the periphery of a plurality of molds 13 put together and on the inside of the mold. Provision of the frame 14 allows a solution of a polymer resin (hereinafter, also referred to as a "polymer solution") to be prevented from flowing to the outside of the mold 13 in the case of forming the functional film to have a desired film thickness.

At this time, the step between the mold 13 and the frame 14 is preferably 50 μm or more and 10 mm or less. In addition, the forms shown in FIGS. 12A and 12B are formed to enable the mold 13 and the frame 14 to be separated from each other, but the mold and the frame can be configured to be integrated together. In the case in which the mold and the frame can be separated from each other, the frame 14 can be removed in a drying step and a peeling-off step following the filling step.

As shown in FIGS. 12C and 12D, a plurality of molds 13 are joined onto a substrate 17 and the plurality of molds 13 are joined to one another, using an adhesive. Then, the frame 14 is installed at the periphery of the side surface of the mold 13 and on the inside of the mold.

Figure 13:
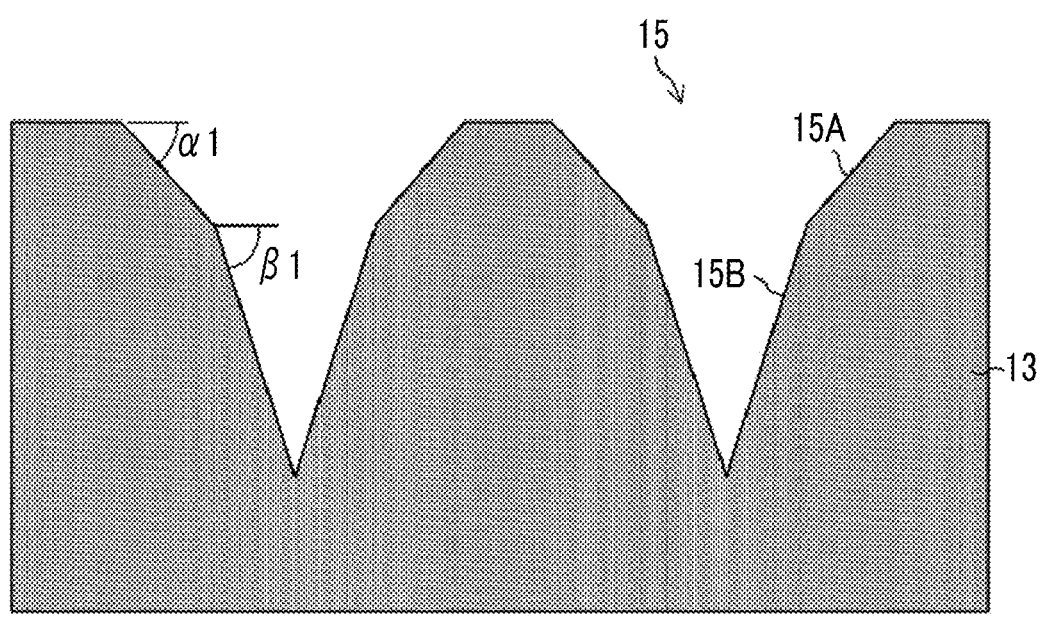
FIG. 13 is an enlarged view of a part of the mold.

FIG. 13 is a partially enlarged view showing the mold 13. The needle-like recessed portion 15 is provided with a tapered inlet portion 15A that is narrower in a depth direction from the surface of the mold 13, and a tip end recessed portion 15B that is tapered in the depth direction. The angle α1 of the taper of the inlet portion 15A basically coincides the angle α formed between the side surface of the frustum portion of the transdermal absorption sheet and the sheet portion. In addition, the angle β1 of the taper of the tip end recessed portion 15B basically coincides the angle β formed between the side surface of the needle portion and the upper base of the frustum portion.

Figure 14:
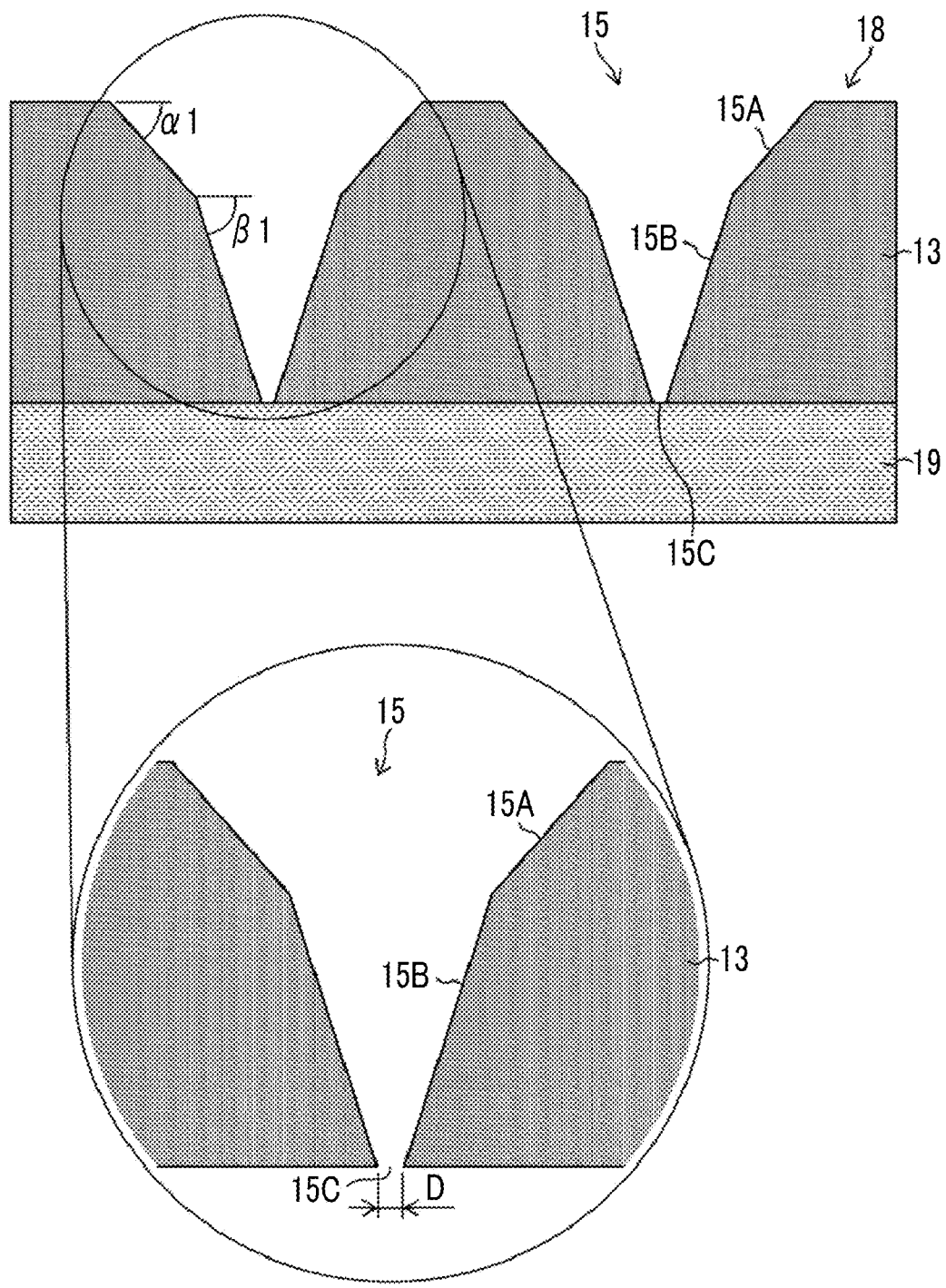
FIG. 14 is a partially enlarged view of a mold complex.

FIG. 14 shows a more preferred embodiment of a mold complex 18 in performing a method of producing a transdermal absorption sheet. As shown in FIG. 14, the mold complex 18 includes a mold 13 in which a through-hole 15C is formed at the tip end of the needle-like recessed portion 15 and a gas permeable sheet 19 that is bonded to the side of the through-hole 15C of the mold 13 and is made of a material that is gas permeable, but is not liquid permeable. Through the through-hole 15C, the tip end of the needle-like recessed portion 15 communicates with the atmosphere through the gas permeable sheet 19. The expression "tip end of the needle-like recessed portion 15" means a side that is tapered in a depth direction of the mold 13 and is opposite to the side from which a drug solution that is a base solution is poured.

Using such a mold complex 18, only the air present in the needle-like recessed portion 15 can be removed from the needle-like recessed portion 15 via the through-hole 15C without permeation of the transdermal absorption material solution filling in the needle-like recessed portion 15. The transferability in the case in which the shape of the needle-like recessed portion 15 is transferred to the transdermal absorption material is improved, and thus it is possible to form a sharper needle-like protruding portion.

The diameter D of the through-hole 15C is preferably in a range of 1 to 50 μm. By adjusting the diameter within this range, air bleeding is easily performed, and the tip end portion of the needle-like protruding portion of the transdermal absorption sheet can be formed into a sharp shape. As the gas permeable sheet 19 made of a material that is gas permeable, but is not liquid permeable, for example, PORE-FLON (registered trademark, manufactured by Sumitomo Electric Industries, Ltd.) can be suitably used.

As the material used for the mold 13, an elastic raw material and a metallic raw material can be used. Of these, an elastic raw material is preferable and a raw material with high gas permeability is more preferable. The oxygen permeability, which is representative of the gas permeability, is preferably more than $1 \times 10^{-12}$ (mL/s·m·Pa) and more preferably more than $1 \times 10^{-10}$ (mL/s·m·Pa). By setting the gas permeability to be in the above range, the air present in the needle-like recessed portion 15 of the mold 13 can be removed from the mold 13. It is possible to produce a transdermal absorption sheet with few defects. Specific examples of such a material include materials obtained by melting general engineering a silicone resin (for example, SYLGARD 184 (registered trademark) or 1310ST), an ultraviolet curable resin, or a plastic resin (for example, polystyrene or polymethylmethacrylate (PMMA)) and materials obtained by dissolving any of the above resins in a solvent. Among these, a silicone rubber-based raw material can be suitably used because of the durability thereof to transfer by repeated pressurization and the good peelability thereof from the raw material. In addition, examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX material (registered trademark), chrome alloy stainless tool steel), and alloys thereof. As the material for the frame 14, the same material as the material of the mold 13 can be used.

(Polymer Solution)

The polymer solution that is a solution of the polymer resin used in the embodiment is described.

In the embodiment, the expression "polymer solution containing the drug" or "drug-containing solution" means a polymer solution containing a predetermined amount of drug or a solution containing a predetermined amount of drug. In addition, the expression "polymer solution not containing the drug" or "non-drug-containing solution" means a polymer solution not containing a predetermined amount of drug or a solution not containing a predetermined amount of drug.

Further, the polymer solution containing a drug is referred to as a drug solution and the polymer solution not containing a drug is referred to as a base solution in some cases.

Whether or not a predetermined amount of drug is contained in the solution can be determined based on whether or not the effect of the drug can be exhibited in the case in which the transdermal absorption sheet punctures the body surface. Accordingly, the expression "containing a predetermined amount of drug" means containing the drug in such an amount that the effect of the drug is exhibited in the case in which the transdermal absorption sheet punctures the body surface. The expression "not containing a predetermined amount of drug" means not containing the drug in such an amount that the effect of the drug is exhibited. The range of the amount of the drug includes a range from 0, at which the drug is not contained, to the amount of the drug at which the effect of the drug is exhibited.

As the raw material for the resin polymer used for the polymer solution, a biocompatible resin is preferably used. It is preferable to use, as such a resin, sugar such as glucose, maltose, pullulan, chondroitin sulfate, sodium hyaluronate, hydroxyethyl starch or hydroxypropyl cellulose, protein such as gelatin, or a biodegradable polymer such as polylactic acid and a lactic acid-glycolic acid copolymer. Among these, gelatin-based raw materials can be suitably used since the gelatin-based raw materials have adhesiveness with many base materials and have a high gel strength as materials to be gelated, and in the peeling-off step described later, the raw materials can be closely attached to the base material and a polymer sheet can be peeled off from the mold using the base material. The concentration of the resin is preferably such that 10% to 50% by mass of the resin polymer is contained in the polymer solution not containing a drug, while the concentration depends on the kind of the material. Additionally, a solvent used for dissolution may be other than hot water as long as the solvent has volatility, and methyl ethyl ketone, alcohol, or the like may be used. The drug to be supplied to the inside of the human body may concurrently be dissolved into the solution of the polymer resin in accordance with the application. The concentration of the polymer of the polymer solution containing a drug (the concentration of the polymer excluding the drug in the case in which the drug itself is a polymer) is preferably 0% to 40% by mass.

For a method for preparing the polymer solution, in the case in which a water-soluble polymer (gelatin or the like) is used, the solution may be prepared by dissolving water-soluble polymer powder into water, and after the dissolution, adding a drug to the solution or putting and dissolving water-soluble powder into a drug-containing solution dissolved therein. In the case in which the polymer resin is difficult to dissolve into water, the polymer resin may be dissolved on heating. The temperature can be appropriately selected as needed depending on the kind of the polymer material, but the material is preferably heated at about 60° C. or lower. Regarding the viscosity of the solution of the polymer resin, the viscosity of the drug-containing solution is preferably 100 Pa·s or less and more preferably 10 Pa·s or less. The viscosity of the non-drug-containing solution is preferably 2,000 Pa·s or less and more preferably 1,000 Pa·s or less. Appropriate adjustment of the viscosity of the solution of the polymer resin facilitates injection of the solution into the needle-like recessed portions of the mold. For example, the viscosity of the solution of the polymer resin can be measured with a capillary type viscometer, a falling ball type viscometer, a rotational type viscometer, or an oscillatory type viscometer.

(Drug)

The drug that the polymer solution contains is not particularly limited as long as the drug is a substance having bioactivity. The drug is preferably selected from peptide, protein, nucleic acid, polysaccharide, a vaccine, a medical compound, and a cosmetic component. In addition, it is preferable that the medical compound belongs to a water-soluble low-molecular-weight compound. Here, the low-molecular-weight compound refers to a compound in a range of a molecular weight of several hundreds to several thousands.

(Method of Producing Transdermal Absorption Sheet)

Figure 15:
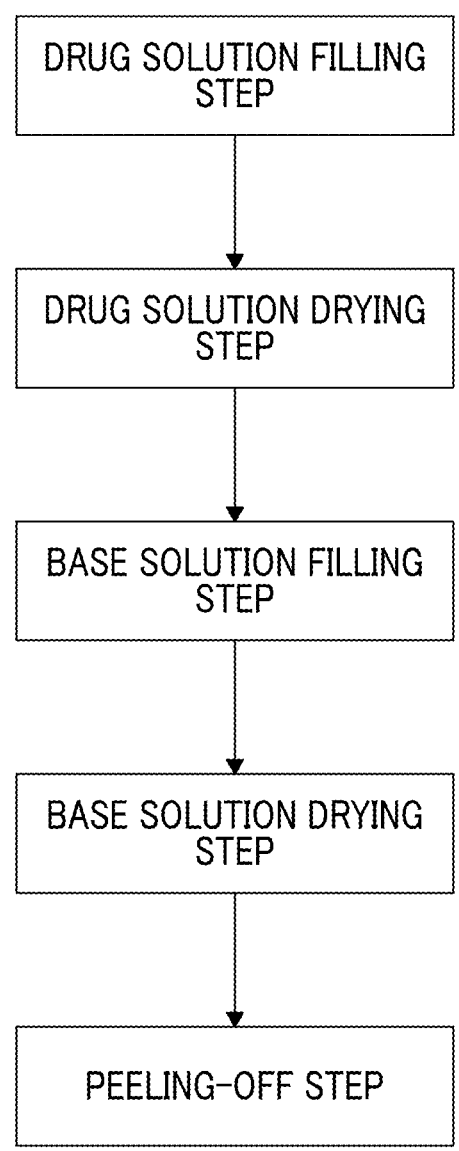
FIG. 15 is a flowchart of a method of producing a transdermal absorption sheet.

The method of producing the transdermal absorption sheet of the embodiment includes at least five steps of a drug solution filling step, a drug solution drying step, a base solution filling step, a base solution drying step, and a peeling-off step in this order as shown in FIG. 15.

(Drug Solution Filling Step)

Figure 16A:
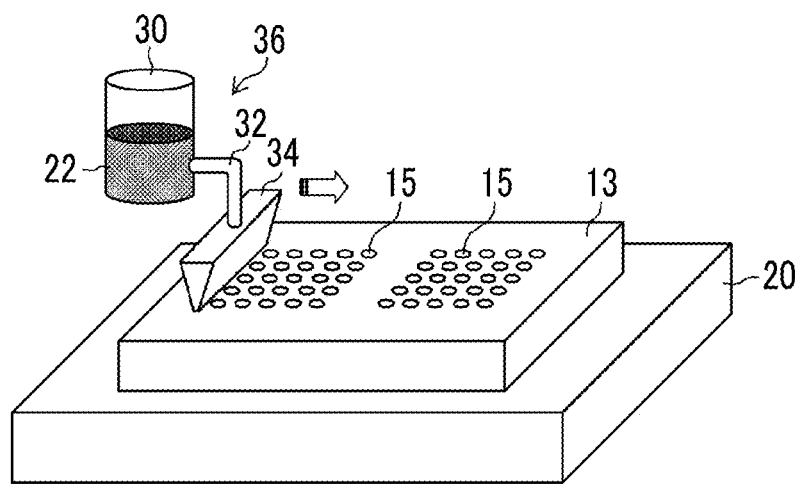
FIG. 16A is a schematic view showing a step of filling a needle-like recessed portion of a mold with a drug solution.

The method of producing the transdermal absorption sheet using the mold 13 will be described. As shown in FIG. 16A, the mold 13 with the two-dimensionally arranged needle-like recessed portions 15 is placed on a base 20. Two sets of a plurality of needle-like recessed portions 15, each set including 5×5 two-dimensionally arranged needle-like recessed portions 15, are formed in the mold 13. A liquid supply apparatus 36 which has a liquid feed tank 30 storing a drug solution 22 that is a polymer solution containing a drug, a pipe 32 connected to the liquid feed tank 30, and a nozzle 34 connected to a tip end of the pipe 32 is prepared. The drug solution 22 is discharged from the tip end of the nozzle 34.

Figure 17:
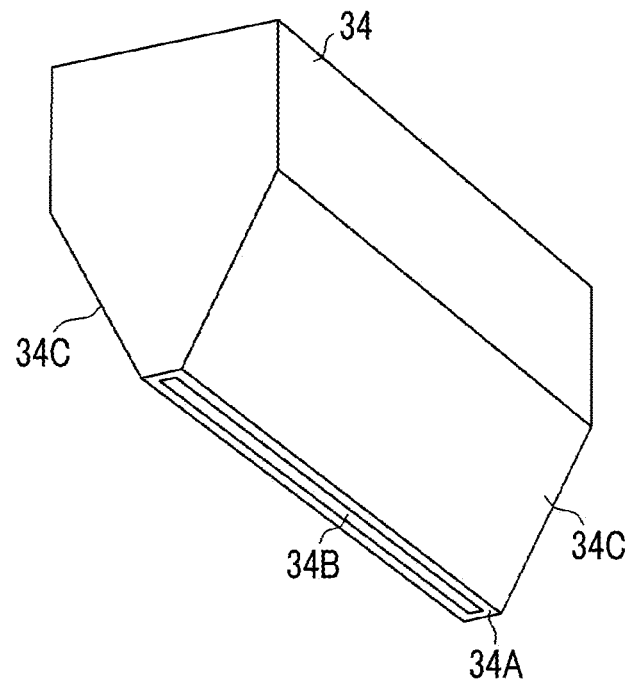
FIG. 17 is a perspective view showing a tip end of a nozzle.

FIG. 17 shows a schematic perspective view of the tip end portion of the nozzle. As shown in FIG. 17, the nozzle 34 includes a lip portion 34A that has a flat surface on the tip end side, a slit-shaped opening portion 34B, and two inclined surfaces 34C that are widened along the lip portion 34A in a direction away from the opening portion 34B. The slit-shaped opening portion 34B, for example, allows a plurality of needle-like recessed portions 15 constituting one column to be simultaneously filled with the drug solution 22. The size (length and width) of the opening portion 34B is appropriately selected in accordance with the number of needle-like recessed portions 15 to be filled at a time.

An increased length of the opening portion 34B makes it possible to fill an increased number of needle-like recessed portions 15 with the drug solution 22 at a time. Thus, productivity can be improved.

Figure 18:
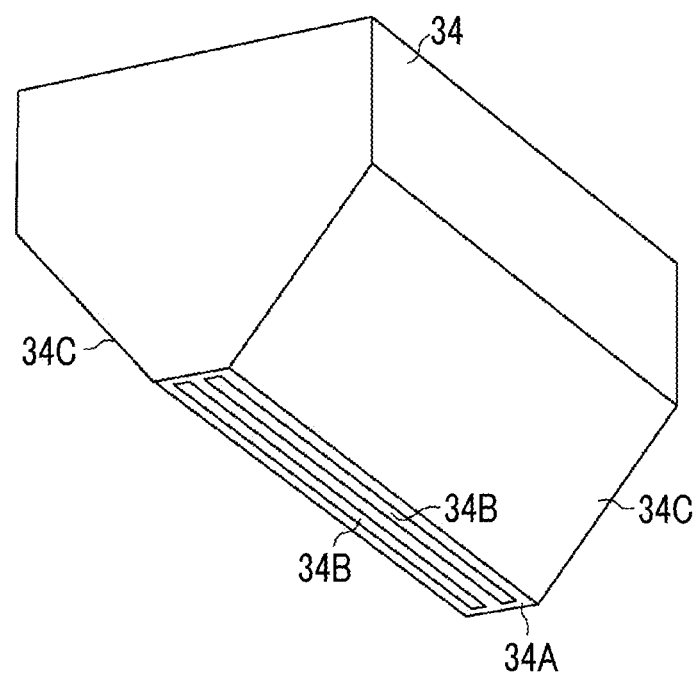
FIG. 18 is a perspective view showing a tip end of another nozzle.

FIG. 18 shows a schematic perspective view of a tip end portion of another nozzle. As shown in FIG. 18, the nozzle 34 has a lip portion 34A having a flat surface on the tip end side, two slit-shaped opening portions 34B, and two inclined surfaces 34C that are widened along the lip portion 34A in a direction away from the opening portion 34B. The two openings portions 34B, for example, allow a plurality of needle-like recessed portions 15 constituting two columns to be simultaneously filled with the drug solution 22 containing a drug.

As the material used for the nozzle 34, an elastic raw material and a metallic raw material may be used. For example, TEFLON (registered trademark), stainless steel, or titanium may be used.

Figure 16B:
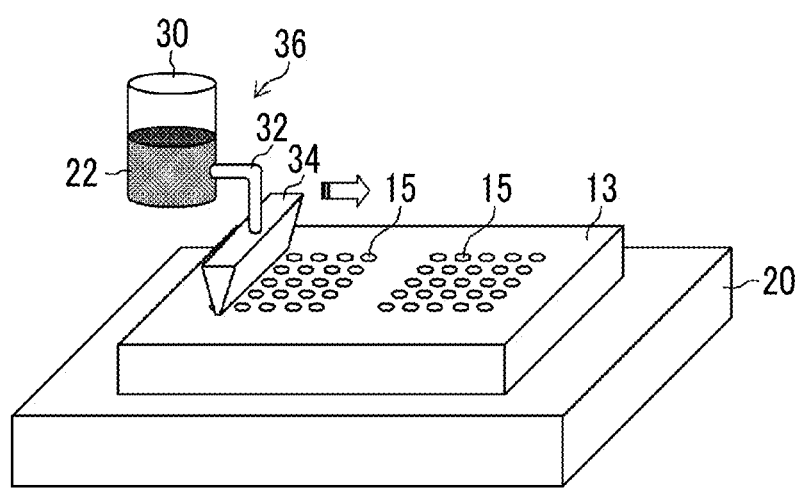
FIG. 16B is a schematic view showing the step of filling the needle-like recessed portion of the mold with the drug solution.

The filling step will be described with reference to FIG. 16B. As shown in FIG. 16B, the position of the opening portion 34B in the nozzle 34 is adjusted on the needle-like recessed portions 15. The lip portion 34A of the nozzle 34 is in contact with the surface of the mold 13 since the nozzle 34 that discharges the drug solution 22 is pressed against the mold 13. The drug solution 22 is supplied from the liquid supply apparatus 36 to the mold 13, and the needle-like recessed portions 15 are filled with the drug solution 22 through the opening portion 34B in the nozzle 34. In the embodiment, the plurality of needle-like recessed portions 15 constituting one column are simultaneously filled with the drug solution 22. However, the present invention is not limited to this configuration. The needle-like recessed portions 15 may be filled with the drug solution 22 one by one. In addition, by using the nozzle 34 shown in FIG. 18, the plurality of needle-like recessed portions 15 constituting the plurality of columns can be simultaneously filled with the drug solution 22 so that filling is performed on the plurality of columns at a time.

In the case in which the mold 13 is formed of a raw material having gas permeability, the drug solution 22 can be sucked by sucking from the back surface of the mold 13, thereby promoting filling of the inside of the needle-like recessed portions 15 with the drug solution 22.

Figure 16C:
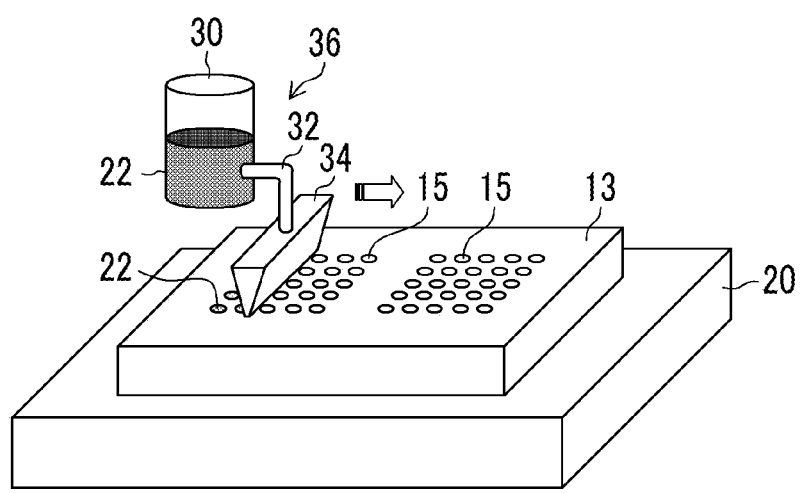
FIG. 16C is a schematic view showing the step of filling the needle-like recessed portion of the mold with the drug solution.

As shown in FIG. 16C, while bringing the lip portion 34A of the nozzle 34 into contact with the surface of the mold 13, the liquid supply apparatus 36 is relatively scanned in a direction perpendicular to a length direction of the opening portion 34B subsequent to the filling step in FIG. 16B. By scanning the surface of the mold 13 by the nozzle 34, the nozzle 34 is moved to the needle-like recessed portion 15 not filled with the drug solution 22. The position of the opening portion 34B of the nozzle 34 is adjusted on the needle-like recessed portions 15. The embodiment has been described with reference to the example in which the nozzle 34 is scanned. However, the mold 13 may be scanned.

Since the nozzle 34 is scanned on the surface of the mold 13 while the lip portion 34A of the nozzle 34 is brought into contact the surface of the mold 13, the nozzle 34 can scrape off the drug solution 22 remaining on the surface of the mold 13 excluding the needle-like recessed portions 15. This enables the drug solution 22 containing a drug to be prevented from remaining on the surface of the mold 13 excluding the needle-like recessed portions 15. In the embodiment, the inclined surfaces 34C of the nozzle 34 are arranged at a position perpendicular to the scanning direction indicated by the arrow. Accordingly, the nozzle 34 can be smoothly scanned on the surface of the mold 13.

In order to reduce damage to the mold 13 and to suppress deformation of the mold 13 due to compression as much as possible, the degree of pressurization of the nozzle 34 against the mold 13 in the case of scanning is preferably controlled. For example, the pressing force with which the nozzle 34 is pressed against the mold 13 or the pressing distance of the nozzle 34 against the mold 13 is preferably controlled. Furthermore, in order to prevent the drug solution 22 from remaining on the mold 13 excluding the needle-like recessed portions 15, at least one of the mold 13 or the nozzle 34 is desirably formed of a flexible, elastically deformable raw material.

The filling step shown in FIG. 16B and the moving step shown in FIG. 16C are repeated to fill a 5×5 two-dimensionally arranged needle-like recessed portions 15 with the drug solution 22. In the case in which the 5×5 two-dimensionally arranged needle-like recessed portions 15 are filled with the drug solution 22, the liquid supply apparatus 36 is moved to the adjacent 5×5 two-dimensionally arranged needle-like recessed portions 15, and the filling step in FIG. 16B and the moving step in FIG. 16C are repeated. The adjacent 5×5 two-dimensionally arranged needle-like recessed portions 15 are also filled with the drug solution 22.

The above filling step and scanning step may be in (1) a form in which the needle-like recessed portions 15 are filled with the drug solution 22 while the nozzle 34 is being scanned or (2) a form in which, while the nozzle 34 is in scanning, the nozzle 34 is temporarily stopped above the needle-like recessed portions 15 to fill the needle-like recessed portions 15 with the drug solution 22, and the nozzle 34 is scanned again after the filling. Between the filling step and the scanning step, the lip portion 34A of the nozzle 34 is pressed against the surface of the mold 13. The amount of the drug solution 22 discharged from the liquid supply apparatus 36 is preferably equal to the total volume of the plurality of needle-like recessed portions 15 of the mold 13 to be filled. The drug solution 22 is prevented from remaining on the surface of the mold 13 excluding the needle-like recessed portions 15 and thus wasting the drug can be reduced.

Figure 19:
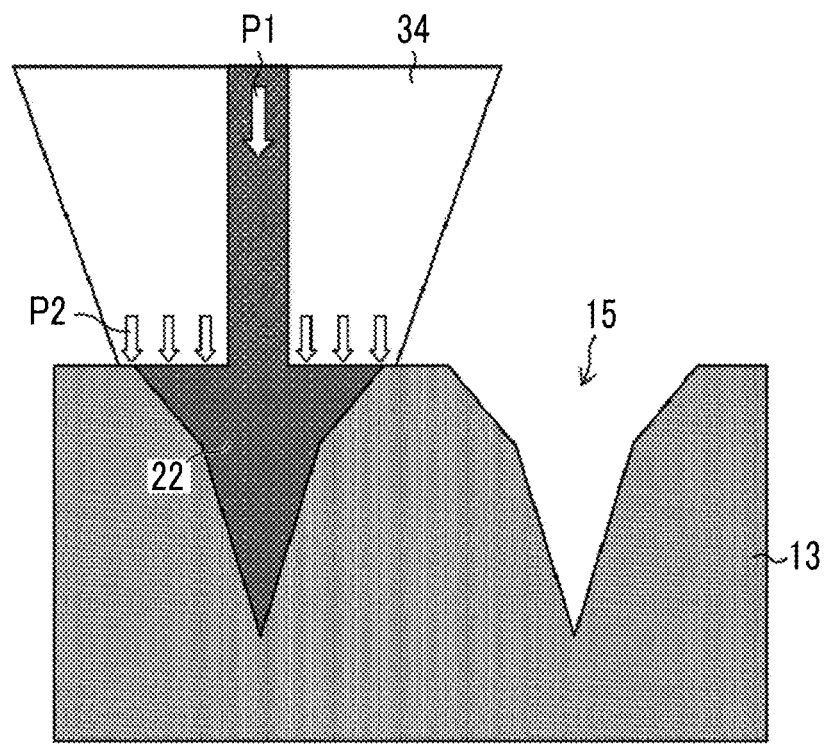
FIG. 19 is a partially enlarged view showing the tip end of the nozzle and the mold during filling.

FIG. 19 is a partially enlarged view of the tip end of the nozzle 34 and the mold 13 during filling of the needle-like recessed portions 15 with the drug solution 22. As shown in FIG. 19, filling of the inside of the needle-like recessed portions 15 with the drug solution 22 can be promoted by applying a pressuring force P1 into the nozzle 34. Moreover, in the case in which the needle-like recessed portions 15 is filled with the drug solution 22, a pressing force P2 with which the nozzle 34 is brought into contact with the surface of the mold 13 is preferably set to be equal to or greater than the pressuring force P1 in the nozzle 34. Setting the pressing force P2≥the pressuring force P1 enables the drug solution 22 to be restrained from leaking from the needle-like recessed portions 15 to the surface of the mold 13.

Figure 20:
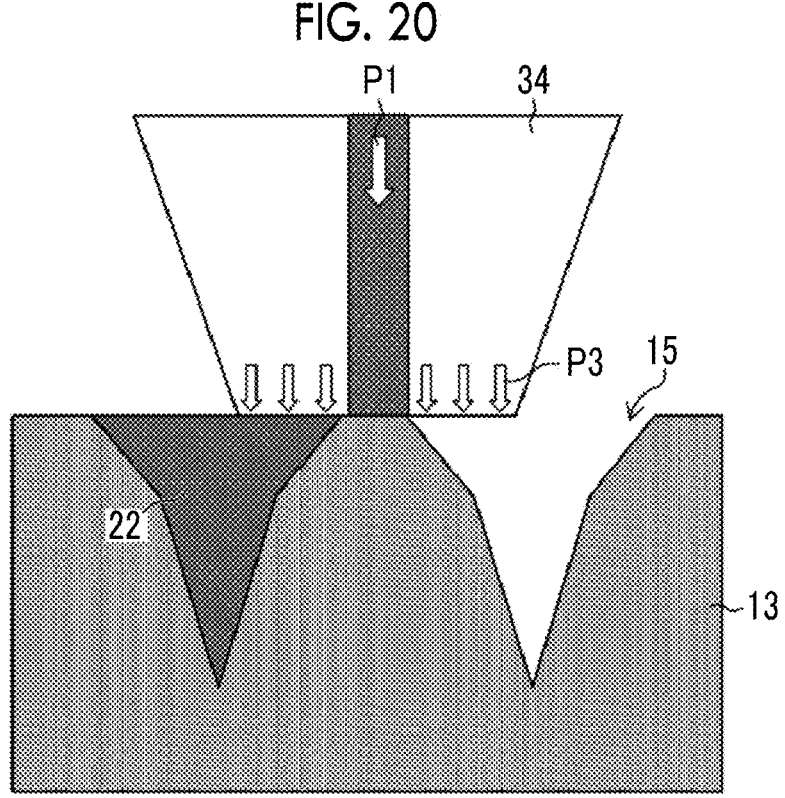
FIG. 20 is a partially enlarged view showing the tip end of the nozzle and the mold during scanning.

FIG. 20 is a partially enlarged view of the tip end of the nozzle 34 and the mold 13 during movement of the nozzle 34. In the case in which the nozzle 34 is scanned relative to the mold 13, a pressing force P3 with which the nozzle 34 is brought into contact with the surface of the mold 13 is preferably set to be smaller than the pressing force P2 with which the nozzle 34 is brought into contact with the surface of the mold 13 while filling is performed. This is intended to reduce damage to the mold 13 and to suppress deformation of the mold 13 associated with compression.

It is preferable that the lip portion 34A of the nozzle 34 is parallel to the surface of the mold 13. The posture of the nozzle 34 may be controlled by providing a joint driving mechanism at a mounting portion of the nozzle 34.

Figure 21:
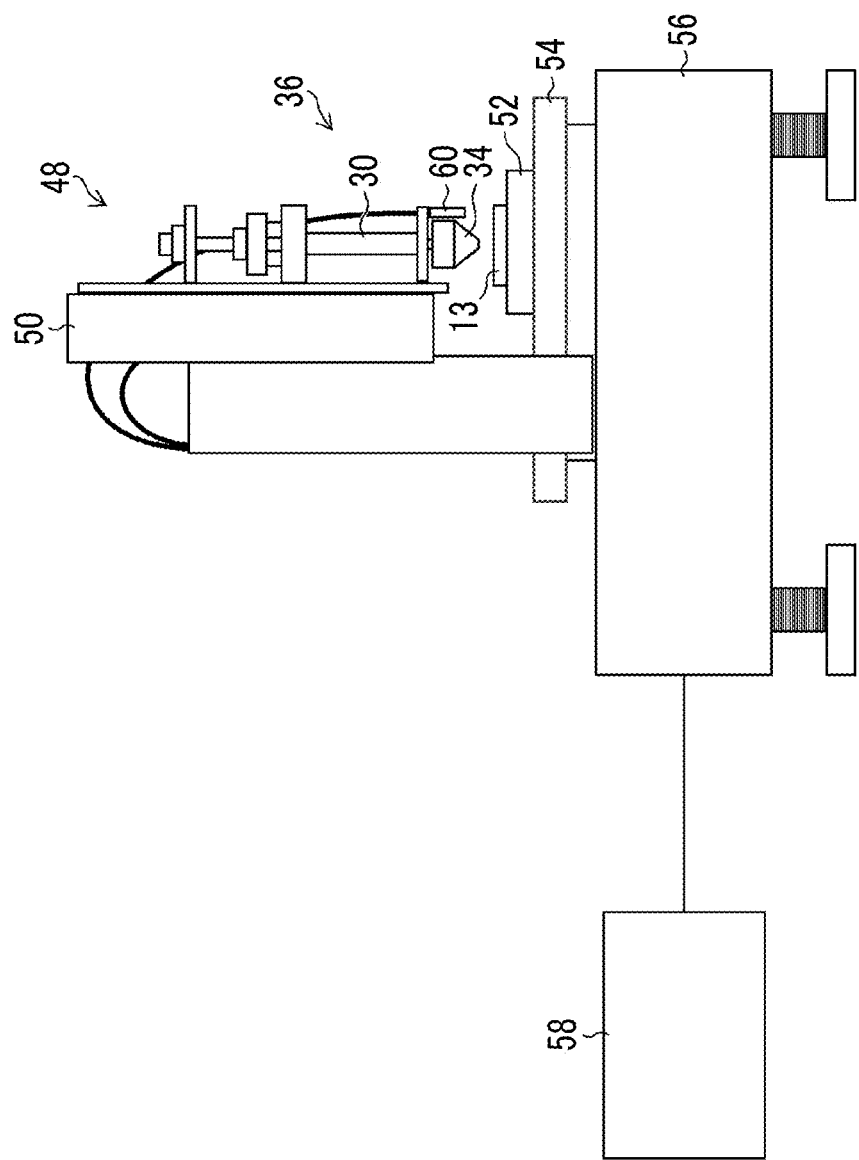
FIG. 21 is a schematic configuration view showing a drug solution filling apparatus.

The pressing force and/or the pressing distance of the nozzle 34 to the mold 13 is/are preferably controlled by driving the nozzle 34 in a Z-axis direction in accordance with the surface shape of the mold 13. FIG. 21 is a schematic configuration diagram of a drug solution filling apparatus 48 capable of controlling the pressing force and/or the pressing distance. The drug solution filling apparatus 48 has a liquid supply apparatus 36 that has a liquid feed tank 30 storing a drug solution and a nozzle 34 mounted on the liquid feed tank 30, a Z-axis driving unit 50 that drives the liquid feed tank 30 and the nozzle 34 in the Z-axis direction, a suction base 52 for placing the mold 13 thereon, a X-axis driving unit 54 that drives the suction base 52 in a X-axis direction, a stand 56 that supports the apparatus, and a control system 58.

The case of controlling a pressing force to be constant will be described. The Z-axis driving unit 50 brings the nozzle 34 close to the mold 13 up to Z-coordinates in which a desired pressing force is obtained. While the nozzle 34 brought into contact with the mold 13 is scanned by the X-axis driving unit 54, the drug solution 22 is discharged while Z-axis coordinate control is performed such that the pressing force becomes constant. The contact pressure measuring method is not particularly limited, but for example, various load cells can be used, for example, under the suction base 52 or in place of the suction base 52. The load cell means a measuring instrument capable of measuring a force for compression in a thickness direction. The pressing force is an arbitrary pressure within a range of 1 to 1,000 kPa with respect to the mold 13, and is preferably controlled to be constant.

The case of controlling a pressing distance to be constant will be described. Before contact with the nozzle 34, the surface shape of the mold 13 is measured in advance. While the nozzle 34 brought into contact with the mold 13 is scanned by the X-axis driving unit 54, the value obtained by performing Z-axis coordinate offset such that a desired pressing distance is provided with respect to the surface shape of the mold 13 is supplied back to the Z-axis driving unit 50 by the control system 58.

The shape measuring method is not particularly limited. For example, an optical measuring instrument such as a non-contact-type laser displacement meter 60 or a contact-type probe-type step profiler can be used. Furthermore, the posture of the nozzle 34 in a slit direction may be controlled in accordance with the surface shape of the mold 13. The pressing distance is preferably controlled within a range of 1% to 15% with respect to the thickness of the mold 13. Through the operation with the control of the distance between the nozzle 34 and the mold 13 in the Z-axis direction by the Z-axis driving unit 50 in accordance with the shape of the mold 13, the compression deformation rate becomes uniform, and thus the accuracy of the filling amount can be improved.

Regarding the control of the pressing force and the pressing distance, the pressing force is preferably controlled in the case in which the pressing distance is small, and the pressing distance is preferably directly controlled in the case in which the pressing distance is large.

FIG. 22 is an illustration for illustrating the relationship between the liquid pressure in the nozzle and the supply of the drug-containing solution. As illustrated in FIG. 22, the supply of the drug solution 22 is started before the nozzle 34 is positioned above the needle-like recessed portions 15. The reason for this is to securely fill the needle-like recessed portions 15 with the drug solution 22. Until the filling of the plurality of needle-like recessed portions 15 of 5×5 is completed, the drug solution 22 is continuously supplied to the mold 13. The supply of the drug solution 22 to the mold 13 is stopped before the nozzle 34 is positioned above needle-like recessed portions 15 in the fifth column. Therefore, it is possible to prevent the drug solution 22 from overflowing from the needle-like recessed portions 15. The liquid pressure in the nozzle 34 increases in a region where the nozzle 34 is not positioned above the needle-like recessed portions 15 in the case in which the supply of the drug solution 22 is started. Meanwhile, in the case in which the nozzle 34 is positioned above the needle-like recessed portions 15, the needle-like recessed portions 15 are filled with the drug solution 22, and the liquid pressure in the nozzle 34 decreases. That is, the liquid pressure repeatedly changes.

In the case in which the filling of the plurality of needle-like recessed portions 15 of 5×5 is completed, the nozzle 34 is moved to a plurality of adjacent needle-like recessed portions 15 of 5×5. Regarding the liquid supply, the supply of the drug solution 22 is preferably stopped in the case in which the nozzle is moved to the plurality of adjacent needle-like recessed portions 15 of 5×5. There is a distance between the needle-like recessed portions 15 in the fifth column and the needle-like recessed portions 15 in the next first column. In the case in which the drug solution 22 is continuously supplied therebetween during the scanning of the nozzle 34, the liquid pressure in the nozzle 34 may excessively increase. As a result, the drug solution 22 may flow to a region of the mold 13 excluding the needle-like recessed portions 15 from the nozzle 34. In order to suppress this problem, the supply of the drug solution 22 is preferably stopped.

The tip end of the nozzle 34 is preferably used after being cleaned in the case of performing the drug solution filling. This is because the accuracy of the filling amount of the drug solution 22 is reduced in a case in which a substance adheres to the surface of the lip portion 34A of the nozzle 34 before filling. In general, wiping using non-woven cloth is performed for cleaning. During wiping, the cleaning can be effectively performed in the case in which non-woven cloth is permeated with water, a solvent, or the like. After filling with the drug solution 22, there is a possibility that the drug solution may remain on the surface of the mold 13 in the case in which the nozzle 34 is separated from the mold 13. By performing suck back control for suction of the drug solution from the opening portion 34B of the nozzle 34 after completion of the filling of the needle-like recessed portions 15, an excessive amount of the drug solution 22 discharged can be sucked, and the liquid remaining on the surface of the mold 13 can thus be reduced.

In the drug solution filling step, the drug solution can be sucked from the through-hole 15C side using the mold complex 18 shown in FIG. 14 to fill the needle-like recessed portions 15 with the drug solution 22. This is because it is not particularly preferable that an air bubble is incorporated in the drug solution 22 since a variation occurs in the content of the drug.

In the case in which the filling of the needle-like recessed portions 15 with the drug solution 22 is completed, the process proceeds to the drug solution drying step, the base solution filling step, the base solution drying step, and the peeling-off step.

Figure 23A:
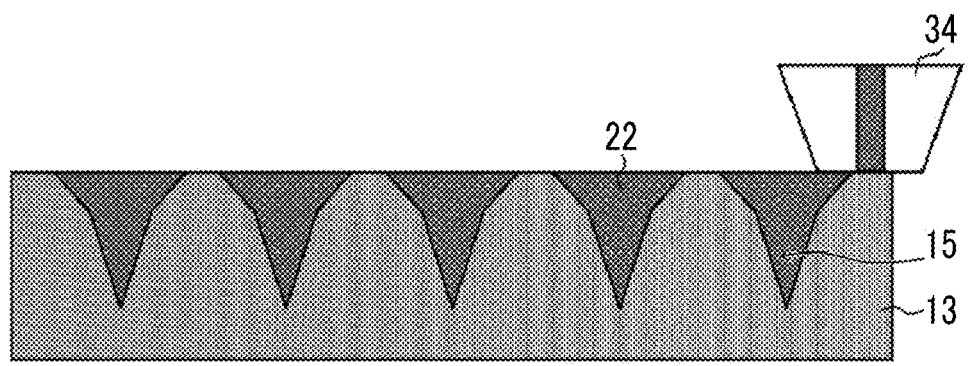
FIG. 23A is a schematic view showing a part of a step of producing a transdermal absorption sheet.

As shown in FIG. 23A, the needle-like recessed portions 15 of the mold 13 are filled with the drug solution 22 from the nozzle 34 in the drug solution filling step. The drug solution filling step is performed using the above-described method.

(Drug Solution Drying Step)

Figure 23B:
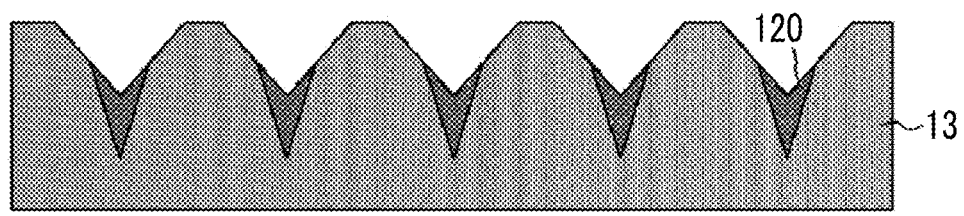
FIG. 23B is a schematic view showing a part of the step of producing a transdermal absorption sheet.

As illustrated in FIG. 23B, in the drug solution drying step, the drug solution 22 is dried and solidified, and thus first layers 120 containing a drug are formed in the needle-like recessed portions 15.

The drug solution drying step is a step of drying the drug solution 22 filled in the needle-like recessed portions 15 of the mold 13 and localizing the first layers 120 containing a drug at the tip ends of the needle-like recessed portions 15. In the embodiment, the drug solution drying step is preferably performed in an environment at a temperature of 1° C. or higher and 10° C. or lower.

In addition, by optimizing the drying rate with the control of the temperature and humidity conditions of the drug solution drying step, it is possible to reduce fixing of the drug solution 22 to a wall surface of the mold 13 of the needle-like recessed portions 15, and the drying proceeds while the drug solution 22 is collected at the tip end of the needle-like recessed portion 15 by drying. For example, in an environment at a temperature of 23° C. and a relative humidity of 40% to 60% RH, the drying rate is high, and thus the drug solution 22 may be fixed to the wall surface of the mold 13 of the needle-like recessed portions 15 and it may be difficult to localize the drug solution 22 at the tip ends of the needle-like recessed portions 15 in some cases.

The drying rate of the drug solution 22 can be reduced by performing the drug solution drying step in an environment at a temperature of 1° C. to 10° C. Accordingly, the drug solution 22 can be localized at the tip ends of the needle-like recessed portions 15 without fixing the drug solution 22 to the wall surface of the mold 13. In the drug solution drying step in an environment at a temperature of 1° C. to 10° C., in the case in which the humidity is high, the drying rate of the drug solution 22 is reduced, and thus deterioration in productivity is caused. In the case in which the drug solution drying step is performed in an environment at a temperature of 1° C. to 10° C., an environment at a relative humidity of 1% to 59% is preferably provided, and an environment at a relative humidity of 21% to 39% is more preferably provided. In an environment in a temperature and humidity range of a temperature of 1° C. to 10° C. and a relative humidity range of 1% to 59%, it is possible to achieve high productivity and the localization of the drug solution 22 at the tip ends of the needle-like recessed portions 15 at the same time.

In order to provide an environment at a relative humidity of 1% to 59%, for example, the drug solution drying step is preferably performed in a constant-temperature chamber or a constant-temperature tank having a humidity adjustment function.

In the drug solution drying step, the drug solution 22 is solidified by being dried, and is reduced compared with that in the case in which the filling with the drug solution 22 is performed. Accordingly, in the peeling-off step, the first layer 120 can be easily peeled off from the needle-like recessed portion 15 of the mold 13.

(Base Solution Filling Step)

Figure 23C:
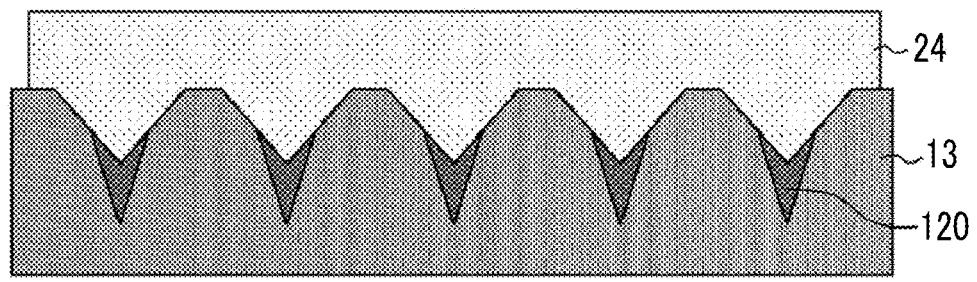
FIG. 23C is a schematic view showing a part of the step of producing a transdermal absorption sheet.

Next, as shown in FIG. 23C, a base solution 24 that is a polymer solution not containing a drug is applied to the first layer 120 containing a drug using a dispenser, and the needle-like recessed portions 15 are filled with the base solution 24. The base solution 24 in an amount larger than the spaces among the needle-like recessed portions 15 fills the needle-like recessed portions. Bar coating, spin coating, coating using a spray, or the like can be applied instead of the application using the dispenser. Since the first layer 120 containing a drug is solidified by drying, diffusion of the drug contained in the first layer 120 into the base solution 24 can be suppressed. The film thickness of the outer edge portion 116B may be controlled by providing distribution in the amount of application at the time of filling with the base solution so that the outer edge portion 116B (refer to FIGS. 7A and 7B) after drying the base solution has a desired shape.

Figure 24A:
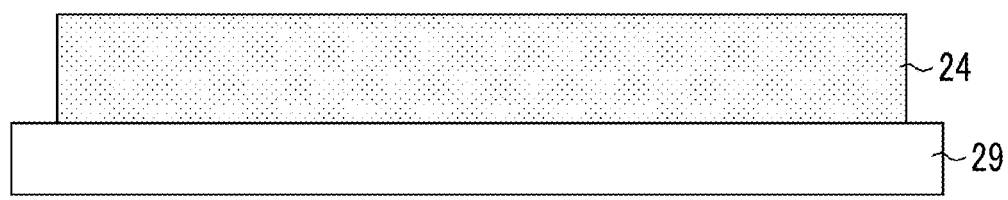
FIG. 24A is a schematic view showing a part of another step of producing a transdermal absorption sheet.
Figure 24B:
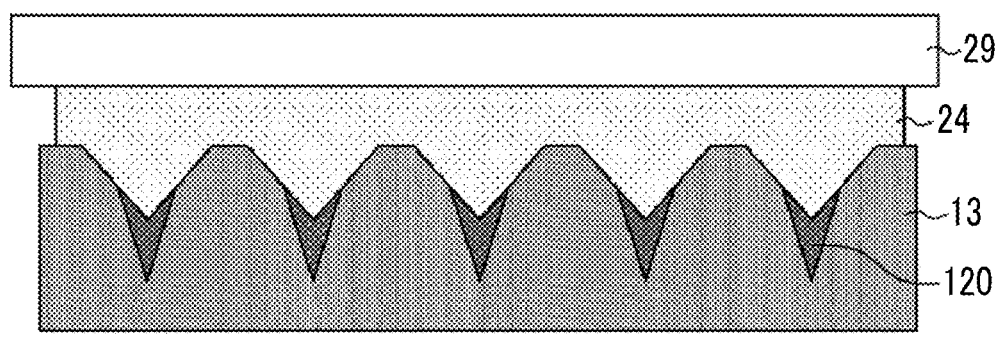
FIG. 24B is a schematic view showing a part of the another step of producing a transdermal absorption sheet.

Next, the base solution filling step of another embodiment will be described. As shown in FIG. 24A, the base solution 24 which is a polymer solution not containing a drug is applied to another support 29. Although the support 29 is not limited, for example, polyethylene, polyethylene terephthalate, polycarbonate, polypropylene, acrylic resin, triacetylcellulose, and the like can be used. Next, as shown in FIG. 24B, the base solution 24 formed on the support 29 is superposed on the mold 13 in which the first layer 120 is formed in the inside of the needle-like recessed portion 15. Thus, the needle-like recessed portion 15 is filled with the base solution 24.

In the embodiment, the base solution filling step includes two steps of a step of applying the base solution 24 on the support 29, and a step of superposing the base solution 24 on the support 29 on the mold 13.

In the embodiment, the first layer 120 is formed and then the upper space of the first layer in the needle-like recessed portion 15 is filled with the base solution 24. Since the first layer 120 is solidified by drying, air bubbles incorporated in the base solution 24 through a gap between the first layer 120 and the surface of the mold 13 and a pin hole of the first layer 120 can be removed from the surface of the needle-like recessed portion 15 of the mold 13 or through-holes in the case of a mold 13 having through-holes.

On the other hand, the case of filling the upper space of the drug solution 22 with the base solution 24 without drying the drug solution 22 will be described. Since the drug solution 22 is a liquid state, there is no gas path such as a gap or pin hole and thus a air bubble escape path is removed. The gas of the base solution 24 is dissolved in the drug solution 22 and the dissolved gas diffuses, for example, from through-holes. Thus, the time for air bubble removal becomes longer. Accordingly, in the case of not drying the drug solution 22, the gas path is limited and thus air bubbles remain in some cases.

That is, formation of the first layer 120 by drying the drug solution 22 facilitates air bubble removal from the base solution 24.

(Base Solution Drying Step)

Figure 23D:
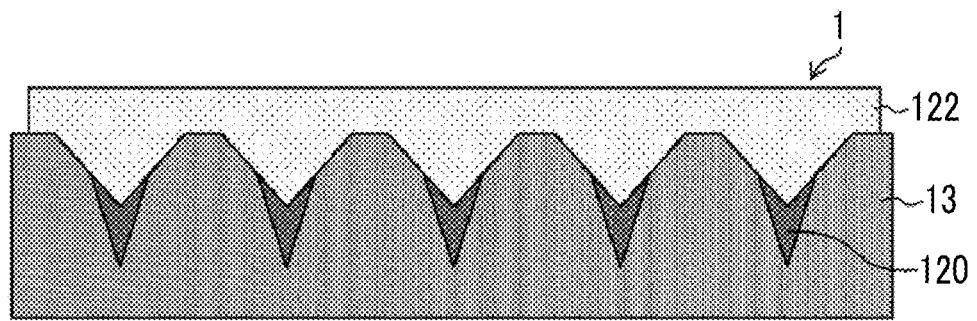
FIG. 23D is a schematic view showing a part of the step of producing a transdermal absorption sheet.

Next, as shown in FIG. 23D, the second layer 122 not containing a drug is formed on the first layer 120 containing a drug by drying and solidifying the base solution 24. A polymer sheet 1 having the first layer 120 and the second layer 122 (before the transdermal absorption sheet 100 is peeled off from the mold 13) is produced.

In the base solution drying step, the volume of the base solution 24 is reduced by drying. Close attachment of the base solution 24 to the mold 13 during the drying leads to a reduction in volume in the film thickness direction of the sheet portion, and thus the film thickness is reduced. In the case in which the base solution 24 is peeled off from the mold 13 during drying, the polymer sheet 1 shrinks in the plane direction and thus the polymer sheet may be deformed or curled. In addition, in the case in which the polymer sheet 1 is peeled off from the mold 13 in a state in which the base solution 24 in the needle-like recessed portion 15 is not sufficiently dried, a defect that the shape of the needle-like protruding portion of the polymer sheet 1 is broken or bent is easily generated. Thus, it is preferable that the polymer sheet 1 is not peeled off from the mold 13 during drying.

In the base solution drying step, it is preferable that the outer edge portion 116B and the thickness portion 116D of the sheet portion 116 and the curved surface of the sheet portion 116 are formed in desired shapes. The following representative methods will be described with reference to FIGS. 25A to 27D. These methods may be carried out alone or in combination thereof. There is no limitation with respect to the following methods and other methods can be used to form a desired shape. In the following description, the peeling-off step and the final drying step, which will be described later, are included.

Figure 25A:
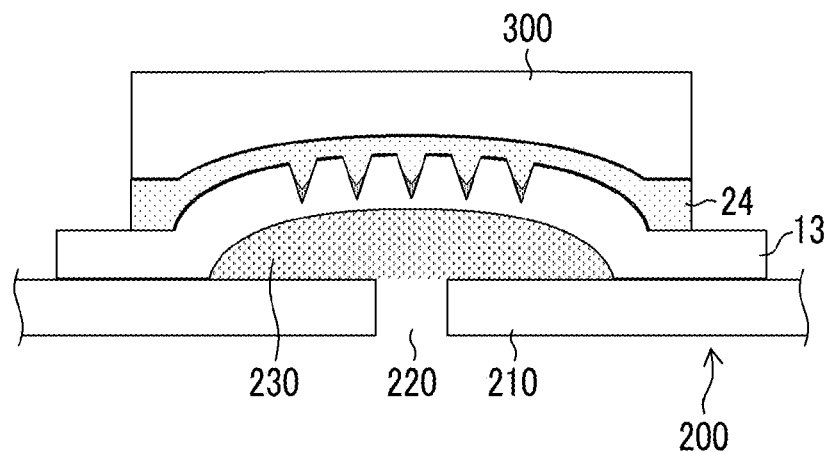
FIG. 25A is a schematic view showing a part of a step of producing a transdermal absorption sheet having a sheet portion having a thickness portion.
Figure 25B:
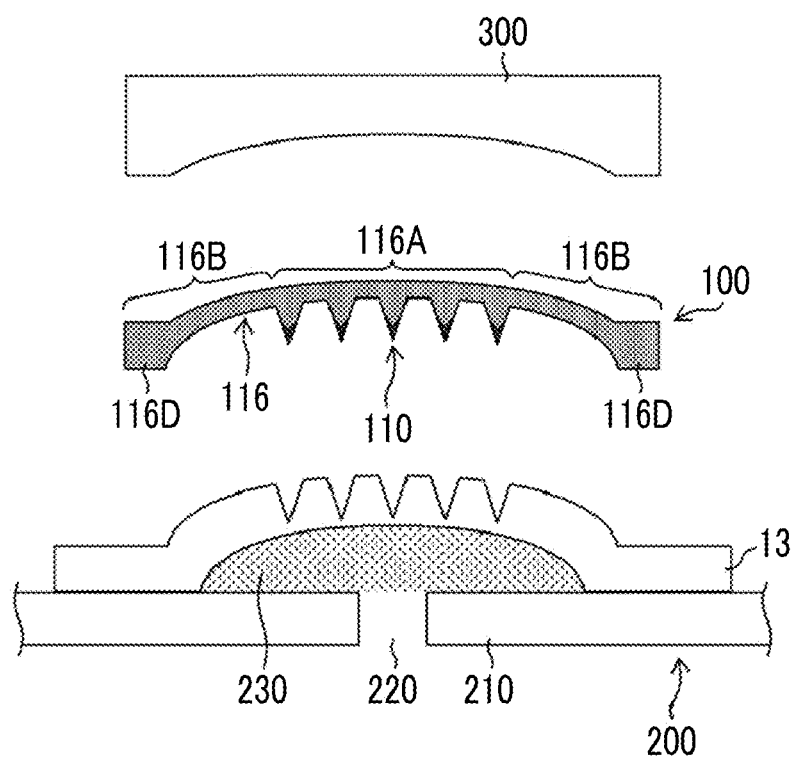
FIG. 25B is a schematic view showing a part of the step of producing a transdermal absorption sheet having a sheet portion having a thickness portion.

FIGS. 25A and 25B show a method of producing a transdermal absorption sheet provided with a sheet portion having a curved shape directed toward a second principal surface from a first principal surface and having a thickness portion in an outer edge portion. As shown in FIG. 25A, a suction apparatus 200 is prepared and the mold 13 filled with the base solution 24 is set to the suction apparatus 200. The suction apparatus 200 has a support base 210 having a suction port 220, and a porous pedestal 230 arranged at a position to cover the suction port 220. The surface shape of the pedestal 230 is processed into the form corresponding to the desired shape of the outer edge portion of the sheet portion in advance.

The tip end side of the needle-like recessed portion of the mold 13 and the pedestal 230 are arranged to face each other and the mold 13 is fixed to the pedestal 230. In the embodiment, suction is performed from the suction port 220 to fix the mold 13 to the pedestal 230. As the porous pedestal 230, a sintered metal compact or a mesh structure can be employed.

Since the mold 13 is formed of an elastic body, the mold is deformed along the shape of the pedestal 230. The method of fixing the mold 13 to the pedestal 230 is not limited to the case of using the suction apparatus 200. In the case of using the support base 210, the mold 13 is preferably fixed to the support base 210 not to be removed by deformation of the mold 13.

A form 300 for forming a second principal surface having a desired shape is arranged on the surface side of the base solution 24 (on the side on which the second principal surface is formed).

As shown in FIG. 25B, while the mold 13 filled with the base solution 24 is fixed with the pedestal 230 and the form 300, drying is performed. Thus, it is possible to produce a transdermal absorption sheet 100 including a sheet portion 116 having an outer edge portion 116B with a desired shape and a thickness portion 116D.

Figure 26A:
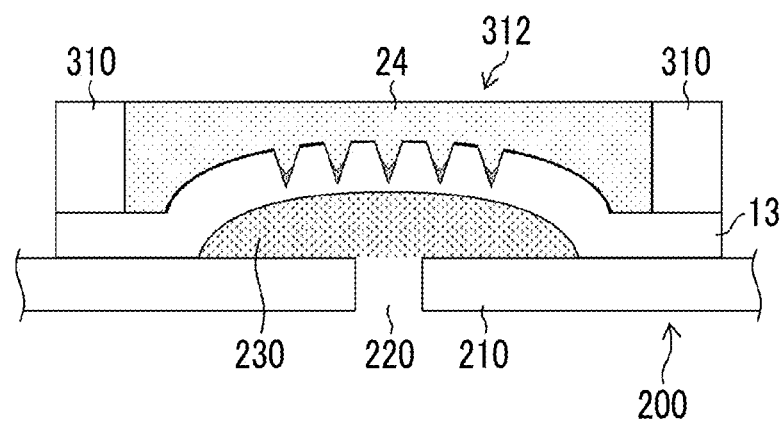
FIG. 26A is a schematic view showing a part of another step of producing a transdermal absorption sheet having a sheet portion having a thickness portion.
Figure 26B:
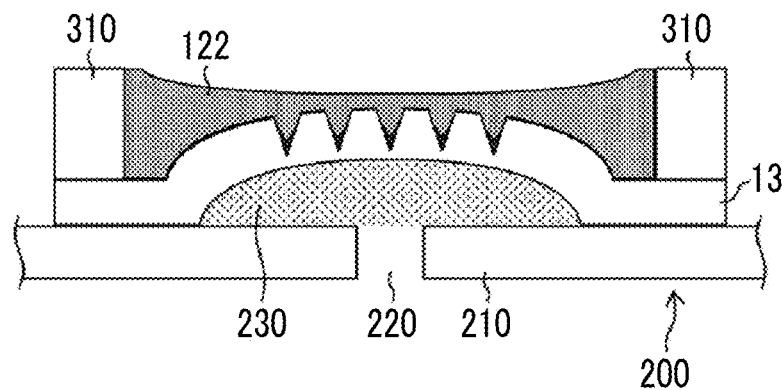
FIG. 26B is a schematic view showing a part of the another step of producing a transdermal absorption sheet having a sheet portion having a thickness portion.
Figure 26C:
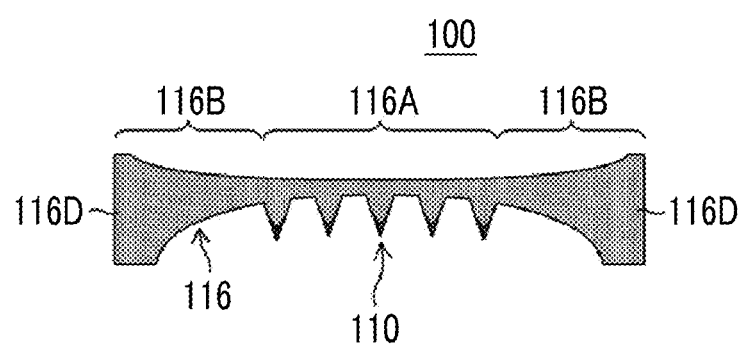
FIG. 26C is a schematic view showing a part of the another step of producing a transdermal absorption sheet having a sheet portion having a thickness portion.

FIGS. 26A to 26C show a method of producing a transdermal absorption sheet having a thickness portion in a first principal surface and a second principal surface. As shown in FIG. 26A, the suction apparatus 200 is prepared and the mold 13 before filling is set to the suction apparatus 200. A form 310 for forming a second principal surface having an opening portion 312 is prepared.

The positions of the needle-like recessed portions of the mold 13 and the opening portion 312 are aligned and the form 310 for forming a second principal surface is arranged on the surface of the mold 13 (on the side to be filled with the base solution 24). In this state, the opening portion is filled with the base solution 24 and the form 310 and the side surface of the base solution 24 are brought into contact with each other.

As shown in FIG. 26B, the base solution 24 is dried to dry and reduce the base solution 24. Since the side surface of the base solution 24 is brought into contact with the form 310, the side surface of the base solution 24 is fixed to the form 310 and is not significantly reduced. Accordingly, the central portion of the base solution 24 is reduced into a thin film shape compared to the side surface of the base solution 24.

As shown in FIG. 26C, the transdermal absorption sheet 100 is peeled off from the mold 13. The moisture contents of the first principal surface and the second principal surface of the transdermal absorption sheet 100 are adjusted to be equal and the transdermal absorption sheet 100 is finally dried.

Since there is no moisture content gradient between the first principal surface and the second principal surface, a difference in internal stress between the first principal surface and the second principal surface is not generated and while the shape of the peeled-off transdermal absorption sheet 100 is maintained, drying is completed.

It is possible to produce a transdermal absorption sheet 100 having a thickness portion 116D in an outer edge portion 116B of a sheet portion 116 on the side of a second principal surface.

In FIG. 26B, the case of providing the form 310 on the side surface is described but the form can be further arranged on the surface side of the base solution 24. The base solution 24 can be dried to have a more desirable shape.

FIGS. 27A to 27D show a method of producing a transdermal absorption sheet having a sheet portion with a curved shape by using a curling phenomenon occurring at the time of drying.

The needle-like recessed portion of the mold 13 is filled with the drug solution and then the drug solution is dried to form a first layer at the tip end portion of the needle-like recessed portion of the mold 13.

Figure 27A:
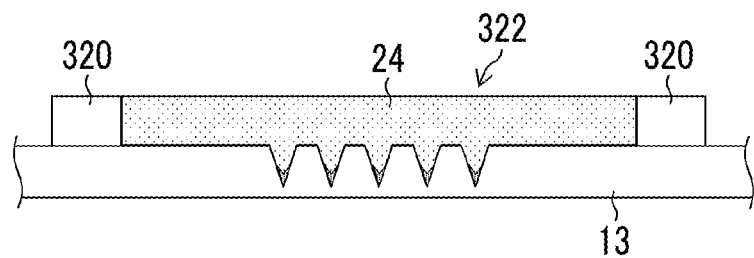
FIG. 27A is a schematic view showing a part of another step of producing a transdermal absorption sheet having a sheet portion having a thickness portion.

As shown in FIG. 27A, the mold 13 having the first layer containing a drug at the tip end portion of the needle-like recessed portion and a form 320 for forming a second principal surface having an opening portion 322 are prepared. The positions of the opening portion 322 and the region of the needle-like recessed portions of the mold 13 are aligned and the form 320 is arranged on the surface of the mold 13. In this state, the opening portion 322 of the form 320 is filled with the base solution 24.

Figure 27B:
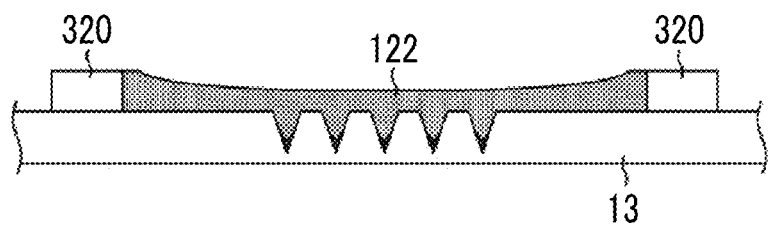
FIG. 27B is a schematic view showing a part of the another step of producing a transdermal absorption sheet having a sheet portion having a thickness portion.

As shown in FIG. 27B, the base solution 24 with which the opening portion 322 of the form 320 is filled is dried. At the time of drying, the moisture content of the surface in contact with the mold 13 and the moisture content of the surface in contact with air are different in the base solution 24. That is, a moisture content gradient is generated in the base solution 24 in the film thickness direction. Due to the moisture content gradient, the base solution 24 has different internal stress (internal stress caused by drying and reduction) in the film thickness direction.

Since the side surface of the base solution 24 is in contact with the form 320 in FIG. 27B, the thickness portion 116D can be formed in the outer edge portion 116B of the sheet portion 116 on the second principal surface side as in the production method shown in FIGS. 26A to 26C.

Figure 27C:
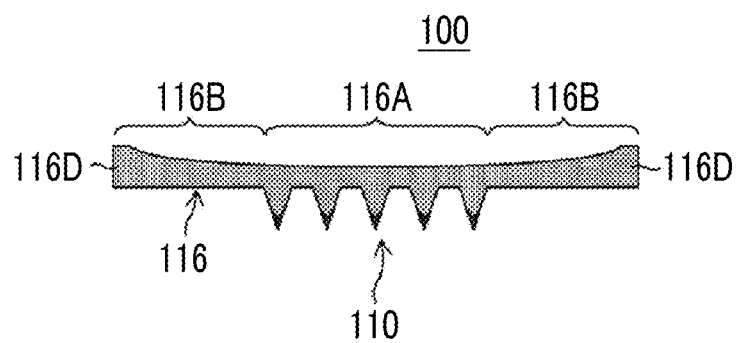
FIG. 27C is a schematic view showing a part of the another step of producing a transdermal absorption sheet having a sheet portion having a thickness portion.

As shown in FIG. 27C, the transdermal absorption sheet 100 is peeled off from the mold 13 and the transdermal absorption sheet 100 is finally dried. In the process of drying, in the case in which the moisture content of the mold 13 increases, the moisture of the first principal surface of the sheet portion 116 with the needle-like protruding portion 110 is evaporated to reduce the base solution 24 after peeling-off. On the other hand, the moisture content of the second principal surface of the sheet portion 116 is low because the second principal surface of the sheet portion is dried in FIG. 27B, and the moisture is hardly evaporated.

Figure 27D:
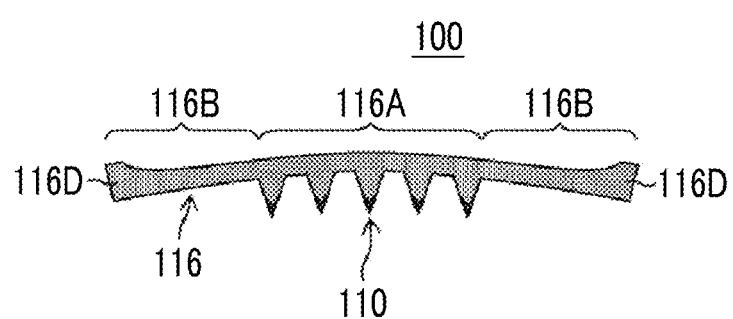
FIG. 27D is a schematic view showing a part of the another step of producing a transdermal absorption sheet having a sheet portion having a thickness portion.

As shown in FIG. 27D, the moisture of the first principal surface of the sheet portion 116 is evaporated and the base solution 24 is further reduced to curl the sheet. Thus, it is possible to produce a transdermal absorption sheet 100 including the sheet portion 116 having a curved shape directed toward the second principal surface from the first principal surface.

That is, a transdermal absorption sheet 100 including the sheet portion 116 having a desired curved shape can be produced through the final drying step after peeling-off by adjusting the moisture content of the base solution 24 in the film thickness direction through control of drying conditions such as temperature, relative humidity, and wind speed.

In the embodiments shown in FIGS. 26A to 27D, since the sheet portion having the outer edge portion having a desired shape and the thickness portion is formed, the method of deforming the mold using the pedestal, the method of bringing the side surface and/or the surface of the base solution into contact with the form, and the method of varying internal stress caused by the moisture content of the base solution in the film thickness direction are exemplified. These methods may be used alone or in combination thereof. The method of forming a desired shape is not limited to these methods and other methods can be used.

(Peeling-Off Step)

Figure 28:
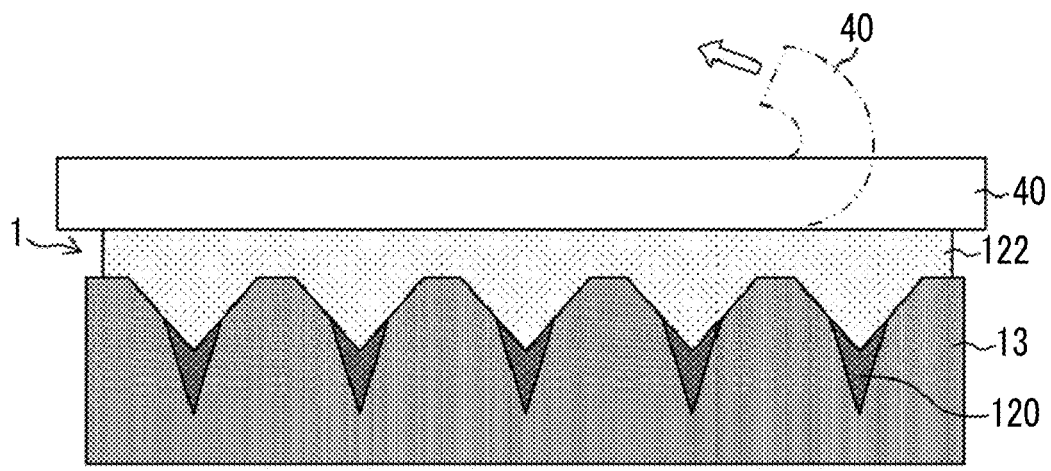
FIG. 28 is an illustration for showing a peeling-off step.
Figure 29:
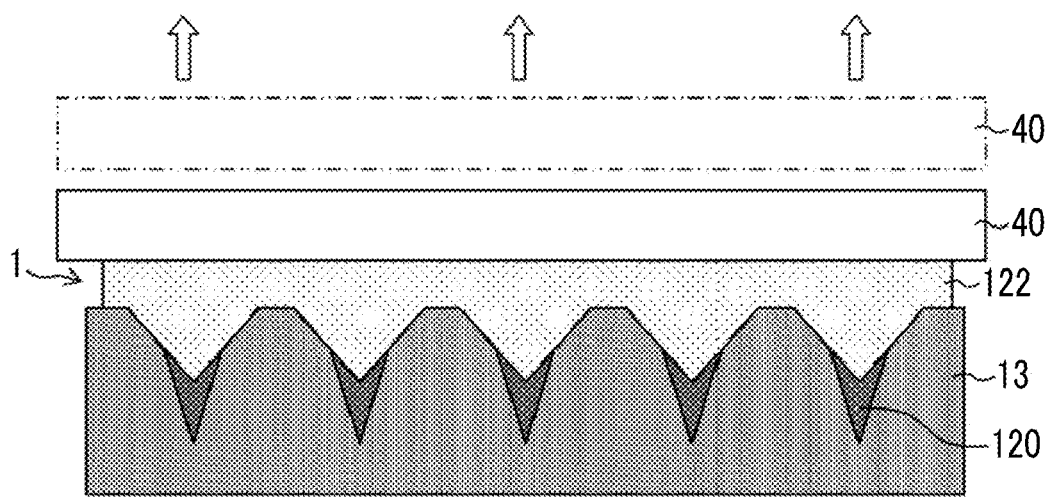
FIG. 29 is an illustration for showing another peeling-off step.

The method of peeling off the polymer sheet 1 from the mold 13 is not limited. It is desirable that the needle-like protruding portion is not bent or broken during peeling-off. Specifically, as shown in FIG. 28, a sheet-like base material 40 in which an adhesive layer having adhesive properties is formed is attached to the polymer sheet 1, and then the base material 40 can be peeled off to be turned over from an end portion. However, in this method, the needle-like protruding portion may be bent. Therefore, a method in which a sucker (not shown) is installed on the back surface of the polymer sheet 1 and it is possible to vertically lift the polymer sheet while sucking the polymer sheet by air as shown in FIG. 29 can be applied. A transdermal absorption sheet 100 is produced by peeling off the polymer sheet 1 from the mold 13.

Usually, in the case in which a structure as a needle-like protruding portion having a high aspect ratio is peeled off from the mold 13 as in this embodiment, a strong stress is applied to the needle-like protruding portion due to a large contact area therebetween. In the case in which the microneedle that is the needle-like protruding portion is broken and thus remains in the needle-like recessed portion 15 without being peeled off from the mold 13, a transdermal absorption sheet to be produced has defects. In this embodiment, the mold 13 is preferably made of a material that is very easily peelable. In addition, the mold 13 is made of a soft material having high elasticity, and thus the stress that is applied to the microneedle during peeling-off can be relaxed.

(Final Drying Step)

The sheet after peeling-off is left to stand in a low humidity environment and dried until the moisture content of the entire sheet reaches 5% or less.

(Deaeration Step)

The drug solution 22 and/or the base solution 24 is/are preferably subjected to deaeration before the drug solution filling step and/or before the base solution filling step. Through deaeration, the air bubbles contained in the drug solution 22 and the base solution 24 can be removed before the filling of the needle-like recessed portion 15 of the mold 13. For example, in the deaeration step, air bubbles having a diameter of 100 μm to several millimeters are removed. By subjecting at least one of the drug solution 22 or the base solution 24 to deaeration, dissolution of the air bubbles in the polymer solution can be promoted.

Examples of the deaeration method include (1) a method of exposing the drug solution 22 under a reduced pressure environment for 1 to 15 minutes, (2) a method of subjecting a container storing the drug solution 22 to ultrasonic vibration for 5 to 10 minutes, (3) a method of applying ultrasonic waves while exposing the drug solution 22 under a reduced pressure environment, and (4) a method of substituting the dissolved gas with helium by sending a helium gas into the drug solution 22. Any of the deaeration methods (1) to (4) also can be applied to the base solution 24.

EXAMPLES

Hereinafter, the present invention will be described in more detail using examples of the present invention. The materials, amounts, ratios, treatment contents, treatment procedures, and the like shown in the following examples can be appropriately changed without departing from the gist of the present invention. Therefore, the scope of the present invention should not be interpreted in a limited manner based on the specific examples illustrated below.

Example 1

(Production of Mold)

Figure 30A:
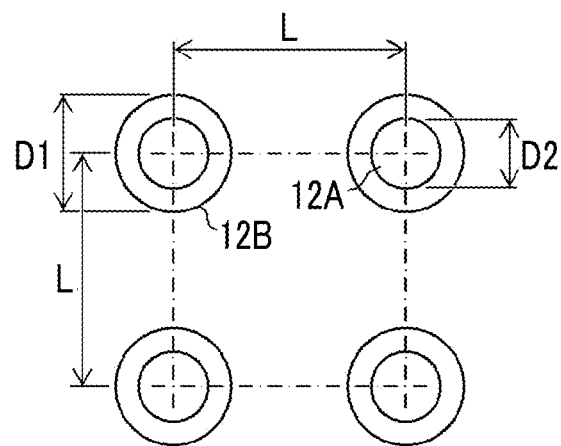
FIG. 30A is a plan view of an original plate.
Figure 30B:
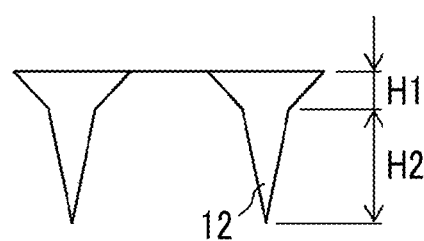
FIG. 30B is a side view of the original plate.

An original plate 11 was produced by subjecting protruding portions 12 each with a needle-like structure to grinding at a pitch L of 1,000 μm in a two-dimensional array with 10 columns and 10 rows on the surface of a smooth Ni plate having one side of 40 mm. As shown in FIGS. 30A and 30B, each protruding portion 12 with a needle-like structure includes a truncated cone 12A with a circular bottom surface having a diameter D1 of 500 μm and a height H1 of 150 μm, and a cone 12B formed on the truncated cone 12A and having a circular bottom surface having a diameter D2 of 300 μm and a height H2 of 500 μm. On the original plate 11, a film with a thickness of 0.6 mm was formed using a silicone rubber (SILASTIC (registered trademark) MDX4-4210, manufactured by Dow Coming Corporation) as a material. The film was thermally cured in a state in which the conical tip end portions of the original plate 11 were projected by 50 μm from the film surface, and then the thermally cured film was peeled off. Accordingly, an inverted article made of silicone rubber having through-holes having a diameter of about 30 μm was produced. The inverted article made of silicone rubber was trimmed so as to leave a planar portion with a side of 30 mm on whose central portion needle-like recessed portions were formed with two-dimensionally arranged in 10 columns and 10 rows and the obtained portion was used as a mold. The surface in which the needle-like recessed portions had wide opening portions served as a surface of the mold, and the surface having through-holes (air vent holes) having a diameter of 30 μm served as a back surface of the mold.

(Preparation of Polymer Solution Containing Drug)

Hydroxyethyl starch (manufactured by Fresenius Kabi) was dissolved in water to prepare an aqueous solution of 8%. To this aqueous solution, 2% by mass of human serum albumin (manufactured by Wako Pure Chemical Industries, Ltd.) as a drug was added to prepare a drug solution containing, a drug. After the solution was prepared, the solution was left to stand for 4 minutes in an environment of a reduced pressure of 3 kPa, and deaeration was performed.

(Preparation of Polymer Solution Not Containing Drug)

Chondroitin sulfate (manufactured by Manilla Nichiro Corporation) was dissolved in water to prepare an aqueous solution of 40% as a polymer solution not containing a drug, that is, a base solution. After the solution was prepared, the solution was left to stand for 4 minutes in an environment at a reduced pressure of 3 kPa, and deaeration was performed.

(Drug Solution Filling Step and Drug Solution Drying Step)

A drug solution filling apparatus is provided with a driving unit that has a X-axis driving unit and Z-axis driving unit controlling relative position coordinates of the mold and the nozzle, a liquid supply apparatus (super small amount fixed-quantity dispenser SMP-III, manufactured by Musashi Engineering, Inc.) on which the nozzle can be mounted, a suction base to which the mold is fixed, a laser displacement meter (HL-C201A, manufactured by Panasonic Corporation) that measures the surface shape of the mold, a load cell (LCX-A-500N, manufactured by Kyowa Electronic Instruments Co., Ltd.) that measures a nozzle pressing pressure, and a control system that controls the Z axis based on data of measured values of the surface shape and the pressing pressure.

A gas permeable film (POREFLON (registered trademark) FP-010, manufactured by Sumitomo Electric Industries, Ltd.) having one side of 15 mm was placed on the flat suction base, and the mold was installed thereon such that the surface thereof was positioned on the upper side. The gas permeable film and the mold were fixed to the vacuum board by pressure reduction with a suction pressure of 90 kPa gauge pressure in the back surface direction of the mold.

A stainless steel nozzle having the shape shown in FIG. 17 was prepared, and a slit-shaped opening portion having a length of 12 mm and a width of 0.2 mm was formed at the center of a lip portion having a length of 20 mm and a width of 0.2 mm. This nozzle was connected to the drug solution tank. The drug solution tank and the nozzle were filled with 3 mL of a solution containing a drug. The nozzle was adjusted such that the opening portion was parallel to the first column of a plurality of needle-like recessed portions formed in the surface of the mold. The nozzle was pressed against the mold at a pressure (pressing force) of 0.14 kgf/cm$^2$ (1.4 N/cm$^2$) at a position apart from the first column with an interval of 2 mm therebetween in a direction opposite to the second column. While being pressed, the nozzle was moved at 1 mm/sec in a direction perpendicular to a length direction of the opening portion while the Z axis was controlled such that the pressing force changed within ±0.05 kgf/cm$^2$ (0.49 N/cm$^2$). Simultaneously, the drug-containing solution was discharged from the opening portion for 10 seconds at 0.31 μL/sec by the liquid supply apparatus. The movement of the nozzle was stopped at a position apart from the tenth column of the plurality of needle-like recessed portions arranged two-dimensionally with an interval of 2 mm therebetween in a direction opposite to the ninth column, and the nozzle was separated from the mold.

The mold filled with the drug solution was left to stand for 30 minutes in an environment at a temperature of 5° C. and a relative humidity of 50% RH and the drug solution was localized at the tip end of the needle-like recessed portion.

(Base Solution Filling Step and Base Solution Drying Step)

A thin stainless steel plate having an opening portion with a diameter of 16 mm and a thickness of 500 μm was prepared as a form. The mold filled with the drug solution was fixed to the suction apparatus by suction. The position of the needle-like recessed portion region of the mold was aligned so as to be in the opening portion of the thin stainless steel plate and the thin stainless steel plate was superposed on the surface of the mold. The base solution was poured into the opening portion of the thin stainless steel plate and an excessive amount of the base solution was scraped off with a squeegee or round bar.

The mold was left to stand to dry the solution for 24 hours in an environment at a temperature of 23° C., a relative humidity of 70% RH, and a wind speed of 0.5 m/s. Due to a low drying rate, the moisture content gradient in the film thickness direction was small.

Since the side surface of the base solution was brought into contact with the thin stainless steel plate, a thickness portion was formed in the contact part of the thin stainless steel plate and the base solution, and the center part of the surface side of the base solution had a small thickness due to drying and reduction. The side of the base solution close to the needle-like protruding portion was formed in a substantially flat shape along the shape of the mold.

(Peeling-Off Step)

The polymer sheet 1 was peeled off from the mold so as to be turned over from the end portion. A transdermal absorption sheet having three-dimensionally arranged needle-like protruding portions each including a layer not containing a drug in which the human serum albumin was unevenly distributed at the tip end, a sheet portion, a second layer not containing a drug arranged on the sheet portion, and a first layer containing a drug was formed. The sheet portion and the second layer not containing a drug were formed of the same material.

(Final Drying Step)

The peeled-off sheet was left to stand in a drying box at a temperature of 23° C. and a relative humidity of 1% RH or lower for 72 hours and the entire sheet portion was dried until the moisture content of the sheet portion reached 5% or less.

(Shape of Transdermal Absorption Sheet)

Since the drying rate was low in the base solution drying step, the moisture content gradient in the film thickness direction was small. Thus, a difference in internal stress in the film thickness direction of the sheet portion, that is, between the first principal surface side and the second principal surface side, was small. Accordingly, the sheet portion was not curled in the final drying step.

After the final drying step, a transdermal absorption sheet having a sheet portion having a first principal surface and a second principal surface, and a plurality of needle-like protruding portions arranged on the first principal surface of the sheet portion was obtained. The first principal surface of the sheet portion was substantially flat and the second principal surface of the sheet portion had a thickness portion on the end portion side of the outer edge portion and was formed in a thin film shape at the central portion by drying and reduction.

Example 2

The same preparation of a polymer solution containing a drug, preparation of a polymer solution not containing a drug, drug solution filling step, drug solution drying step, peeling-off step, and final drying step as in Example 1 were performed except that the base solution filling step and the base solution drying step performed in Example 1 were changed as follows.

(Base Solution Filling Step and Base Solution Drying Step)

A thin stainless steel plate having an opening portion with a diameter of 16 mm and a thickness of 500 μm was prepared as a form. The mold filled with the drug solution was fixed to the suction apparatus by suction. The position of the needle-like recessed portion region of the mold was aligned to be in the opening portion of the thin stainless steel plate, and the thin stainless steel plate was superposed on the surface of the mold. The base solution was poured into the opening portion of the thin stainless steel plate and an excessive amount of the base solution was scraped off with a squeegee or round bar.

The mold was left to stand for 1 hour in an environment at a temperature of 23° C., a relative humidity of 70% RH, and a wind speed of 0.5 m/s to perform primary drying.

Next, a pedestal was prepared to suction the mold. The pedestal is formed of a porous member and has a substantially hemispherical shape having a curved surface having a diameter of 16 mm and a radius of curvature of 40 mm, and a hollow portion in the inside thereof.

Position alignment was performed such that the center of the needle-like recessed portion of the mold was positioned on the curved surface of the hollow portion of the pedestal and the mold was placed on the pedestal to fix the mold by suction. The surface of the tip end side of the needle-like recessed portion of the mold was fixed to the curved surface of the hollow portion of the pedestal. The mold was bent toward the tip end side of the needle-like recessed portion. In this state, the mold was left to stand for 24 hours in an environment at a temperature of 23° C., a relative humidity of 70% RH, and a wind speed of 0.5 m/s to perform secondary drying.

Since the side surface of the base solution was brought into contact with the thin stainless steel plate, a thickness portion was formed in the contact part of the thin stainless steel plate and the base solution, and the center part of the surface side of the base solution was formed to be thinner by drying and reduction. The side of the base solution close to the needle-like protruding portion was formed in a curved shape directed toward the needle-like protruding portion along the shape of the mold.

(Shape of Transdermal Absorption Sheet)

Since the drying rate was low in the base solution drying step, the moisture content gradient in the film thickness direction was small. Thus, a difference in internal stress in the film thickness direction of the sheet portion, that is, between the first principal surface side and the second principal surface side, was small. Accordingly, the sheet portion was not curled in the final drying step.

After the final drying step, a transdermal absorption sheet having a sheet portion having a first principal surface and a second principal surface, and a plurality of needle-like protruding portions arranged on the first principal surface of the sheet portion was obtained.

The sheet portion had a curved shape bent from the second principal surface toward the first principal surface, and the second principal surface of the sheet portion had a thickness portion on the end portion side of the outer edge portion and was formed in a thin film shape at the central portion by drying and reduction. In the case of providing the sheet portion on the same plane, the area of the first principal surface of the sheet portion with the needle-like protruding portions was larger than the projection area as seen from the first principal surface or the second principal surface.

Example 3

The same preparation of a polymer solution containing a drug, preparation of a polymer solution not containing a drug, drug solution filling step, drug solution drying step, peeling-off step, and final drying step as in Example 1 were performed except that the base solution filling step and the base solution drying step performed in Example 1 were changed as follows.

(Base Solution Filling Step and Base Solution Drying Step)

A thin stainless steel plate having an opening portion with a diameter of 16 mm and a thickness of 200 μm was prepared as a form. The mold filled with the drug solution was fixed to the suction apparatus by suction. The position of the needle-like recessed portion region of the mold was aligned to be in the opening portion of the thin stainless steel plate, and the thin stainless steel plate was superposed on the surface of the mold. The base solution was poured into the opening portion of the thin stainless steel plate and an excessive amount of the base solution was scraped off with a squeegee or round bar.

Since the side surface of the base solution was brought into contact with the thin stainless steel plate, a thickness portion was formed in the contact part of the thin stainless steel plate and the base solution, and the center part of the surface side of the base solution was formed to be thinner by drying and reduction. The side of the base solution close to the needle-like protruding portion was formed to be substantially flat along the shape of the mold.

(Shape of Transdermal Absorption Sheet)

Since the drying rate was low in the base solution drying step, a moisture content gradient in the film thickness direction was generated. Due to this moisture content gradient, a difference in internal stress in the film thickness direction of the sheet portion, that is, between the first principal surface side and the second principal surface side, was generated by drying and reduction. Accordingly, the first principal surface side of the sheet portion with the needle-like protruding portion was reduced and the sheet portion was curled in the final drying step.

After the final drying step, a transdermal absorption sheet having a sheet portion having a first principal surface and a second principal surface, and a plurality of needle-like protruding portions arranged on the first principal surface of the sheet portion was obtained.

The sheet portion had a curved shape directed toward the second principal surface from the first principal surface, and the second principal surface of the sheet portion has a thickness portion on the end portion side of the outer edge portion and was formed in a thin film shape at the central portion by drying and reduction. In the case of providing the sheet portion on the same plane, the area of the first principal surface of the sheet portion with the needle-like protruding portions was larger than the projection area as seen from the first principal surface or the second principal surface.

According to Examples 1 to 3, it is possible to produce a transdermal absorption sheet having the sheet portion having a desired shape and having the thickness portion in the outer edge portion, or the sheet portion having a curved shape and having the thickness portion in the outer edge portion.

EXPLANATION OF REFERENCES

1: polymer sheet
11: original plate
12: protruding portion
13: mold
14: frame
15: needle-like recessed portion
15A: inlet portion
15B: tip end recessed portion
15C: through-hole
17: substrate
18: mold complex
19: gas permeable sheet
20: base
22: drug solution
24: base solution
30: liquid feed tank
32: pipe
34: nozzle
34A: lip portion
34B: opening portion
34C: inclined surface
40: base material
36: liquid supply apparatus
48: drug solution filling apparatus
50: Z-axis driving unit
52: suction base
54: X-axis driving unit
56: stand
58: control system
60: laser displacement meter
100: transdermal absorption sheet
110: needle-like protruding portion
112: needle portion
112A: tapered needle-like portion
112B: body portion
114: frustum portion
116: sheet portion
116A: center portion
116B: outer edge portion
116C: end portion
116D: thickness portion
120: first layer
122: second layer
130: skin
200: suction apparatus
210: support base
220: suction port
230: pedestal
300, 310, 320: form
321, 322: opening portion

What is claimed is:

1. A transdermal absorption sheet comprising:
a sheet portion having an end portion and first and second principal surfaces; and
a plurality of needle-shaped protruding portions containing a drug or a cosmetic component arranged on the first principal surface of the sheet portion,
wherein the sheet portion has a center portion which is a region in which the plurality of needle-shaped protruding portions are formed and an outer edge portion which is a region from the center portion to the end portion, and a maximum thickness of a thickness portion of the outer edge portion is larger than an average thickness of the center portion excluding the plurality of needle-shaped protruding portions,
at least a part of a surface on a tip side of each of the plurality of needle-shaped protruding portions are covered with a layer containing the drug or the cosmetic component,
the needle-shaped protruding portion includes a first layer and a second layer, and
the second layer and the sheet portion are formed of the same material.

2. The transdermal absorption sheet according to claim 1, wherein the maximum thickness is 15 μm to 5,000 μm, and the average thickness is 10 μm to 500 μm.

3. The transdermal absorption sheet according to claim 2, wherein the maximum thickness is 1.5 times to 10 times the average thickness.

4. The transdermal absorption sheet according to claim 1, wherein the thickness portion has the maximum thickness in a region of the outer edge portion within 5 mm from the end portion.

5. The transdermal absorption sheet according to claim 1, wherein the thickness portion is provided on the first principal surface and/or the second principal surface of the sheet portion.

6. The transdermal absorption sheet according to claim 1, wherein an area of the first principal surface of the sheet portion is larger than a projection area of the sheet portion as seen from the first principal surface or the second principal surface.

7. The transdermal absorption sheet according to claim 6, wherein the sheet portion has a curved shape directed toward the second principal surface from the first principal surface.

8. The transdermal absorption sheet according to claim 1, wherein the transdermal absorption sheet comprises no adhesive, and
the first layer contains a drug or a cosmetic component, and the second layer does not contain a drug or a cosmetic component.

9. The transdermal absorption sheet according to claim 1, wherein the drug is at least one of peptide, protein, nucleic acid, polysaccharide, a vaccine, or a medical compound.

10. The transdermal absorption sheet according to claim 1, wherein the sheet portion has a circular shape in a plan view, and the thickness portion has the maximum thickness in a region of the outer edge portion within 20% of a diameter of the sheet portion from the end portion.

11. The transdermal absorption sheet according to claim 1,
wherein the thickness portion has the maximum thickness in a region of the outer edge portion within 20% of a length of one side of the sheet portion from the end portion.

* * * * *